(12) United States Patent
Sugiyama et al.

(10) Patent No.: US 10,276,178 B2
(45) Date of Patent: Apr. 30, 2019

(54) SIGNAL PROCESSING APPARATUS, SIGNAL PROCESSING METHOD, AND SIGNAL PROCESSING PROGRAM

(71) Applicant: NEC Corporation, Tokyo (JP)

(72) Inventors: Akihiko Sugiyama, Tokyo (JP); Ryoji Miyahara, Tokyo (JP)

(73) Assignee: NEC Corporation, Tokyo (JP)

( * ) Notice: Subject to any disclaimer, the term of this patent is extended or adjusted under 35 U.S.C. 154(b) by 129 days.

(21) Appl. No.: 14/915,221

(22) PCT Filed: Jun. 16, 2014

(86) PCT No.: PCT/JP2014/065857
§ 371 (c)(1),
(2) Date: Feb. 26, 2016

(87) PCT Pub. No.: WO2015/029545
PCT Pub. Date: Mar. 5, 2015

(65) Prior Publication Data
US 2016/0217803 A1  Jul. 28, 2016

(30) Foreign Application Priority Data

Aug. 30, 2013 (JP) ................................ 2013-180735

(51) Int. Cl.
*G06F 17/00* (2006.01)
*G10L 21/02* (2013.01)
(Continued)

(52) U.S. Cl.
CPC ...... *G10L 21/0205* (2013.01); *A61B 5/04014* (2013.01); *A61B 5/0452* (2013.01);
(Continued)

(58) Field of Classification Search
CPC ..... G10L 25/78; G10L 21/0232; G10L 25/27; G10L 19/025; G10L 21/0205
See application file for complete search history.

(56) References Cited

U.S. PATENT DOCUMENTS 8,194,884 B1 * 6/2012 Johnston ................. H04S 7/30
360/70
2005/0114128 A1 * 5/2005 Hetherington ...... G10L 21/0208
704/233
(Continued)

FOREIGN PATENT DOCUMENTS

JP  2006-163417   6/2006
JP  2011-199808   10/2011
(Continued)

OTHER PUBLICATIONS

"1.5-Mbit/s encoding of video signal and additional audio signal for digital storage media—section 3, audio", JIS X 4323, p. 99, Nov. 1996.
(Continued)

*Primary Examiner* — Fan S Tsang
*Assistant Examiner* — David Siegel
(74) *Attorney, Agent, or Firm* — Finnegan, Henderson, Farabow, Garrett & Dunner, L.L.P.

(57) ABSTRACT

A signal processing apparatus for effectively detecting an abrupt change in a signal, in particular, an abrupt change different from an ideal pulse includes a converter that converts an input signal into a phase component signal in a frequency domain, a first calculator that calculates a phase gradient for each of a plurality of frequencies of the phase component signal as a first phase gradient, a weighting unit that weights the first phase gradient with an amplitude or a power of the input signal, thereby calculating a weighted first phase gradient, a second calculator that calculates a second phase gradient based on the weighted first phase
(Continued)

gradient, and a determiner that determines presence of an abrupt change in the input signal based on the first phase gradient and the second phase gradient.

20 Claims, 22 Drawing Sheets

(51) Int. Cl.
  *A61B 5/0452* (2006.01)
  *A61B 5/04* (2006.01)
  *A61B 5/0456* (2006.01)
  *A61B 5/00* (2006.01)
  *G10L 21/0232* (2013.01)
  *G10L 21/0332* (2013.01)
  *G10L 21/0388* (2013.01)
  *G10L 19/025* (2013.01)

(52) U.S. Cl.
  CPC .......... *A61B 5/0456* (2013.01); *A61B 5/7257* (2013.01); *G10L 21/0232* (2013.01); *G10L 21/0332* (2013.01); *G10L 21/0388* (2013.01); *G10L 19/025* (2013.01)

(56) References Cited

U.S. PATENT DOCUMENTS

| 2005/0199064 A1* | 9/2005 | Wen | G01H 1/00 73/584 |
| 2012/0148067 A1* | 6/2012 | Petersen | H04R 3/005 381/92 |

FOREIGN PATENT DOCUMENTS

| JP | 2011-254122 | 12/2011 |
| JP | 2013-164584 | 8/2013 |

OTHER PUBLICATIONS

M. Kato et al., "Noise suppression with high speech quality based on weighted noise estimation and MMSE STSA", IEICE Trans. Fundamentals (Japanese Edition), vol. J87-A, No. 7, pp. 851-860, Jul. 2004.

R. Martin, "Spectral subtraction based on minimum statistics", EUSPICO-94, pp. 1182-1185, Sep. 1994.

A.D. Cheveigne et al., "YIN, a fundamental frequency estimator for speech and music", J. Acoustic Soc. Amer., vol. 111, No. 4, pp. 1917-1930, Apr. 2002.

J.L. Flanagan et al., "Speech Coding", IEEE Transactions on Communications, vol. 27, No. 4, Apr. 1979.

A. Subramanya et al., "Automatic removal of typed keystrokes from speech signals", IEEE Signal Processing Letters, vol. 14, No. 5, pp. 363-366, May 2007.

J. Murphy et al., "Joint Baysian removal of impulse and background noise", IEEE Proceedings of ICASSP, pp. 261-264, May 2011.

R. Talmon et al., "Transient noise reduction using nonlocal diffusion filters", IEEE Transactions on Audio, Speech, and Language Processing, vol. 19, No. 6, pp. 1584-1599, Jun. 2011.

A. Sugiyama et al., "Impact-noise suppression with phase-based detection", Proc. of IEICE General Conference, p. 73, Mar. 2013.

H. Banno et al., "Efficient Representation of Short-time Phase", IEICE Technical Report SP Onsei, vol. 97, No. 177, pp. 15-20, Jul. 1997.

H. Banno, Efficient Representation of Short-time Phase using Time-domain Smoothed Group Delay and its Evaluation, Report of the Meeting, the Acoustical Society of Japan Autumn I, pp. 209-210, Sep. 1997.

T. Umezaki et al., "Speech Analysis by Group Delay Spectrum of All-Pole Filters and Its Application to the Spectrum Distance Measure for Speech Recognition", The Transactions of the Institute of Electronics, Information and Communication Engineers D-2 Joho System, vol. 72, No. 8, pp. 1141-1150, Aug. 1989.

F. Itakura et al., "Distance Measure for Speech Recognition Based on The Smoothed Group Delay Spectrum", Acoustics, Speech, and Signal Processing, IEEE International Conference on ICASP, vol. 12, pp. 1257-1260, Apr. 1987.

International Search Report and Written Opinion dated Sep. 16, 2014 in corresponding PCT International Application.

* cited by examiner

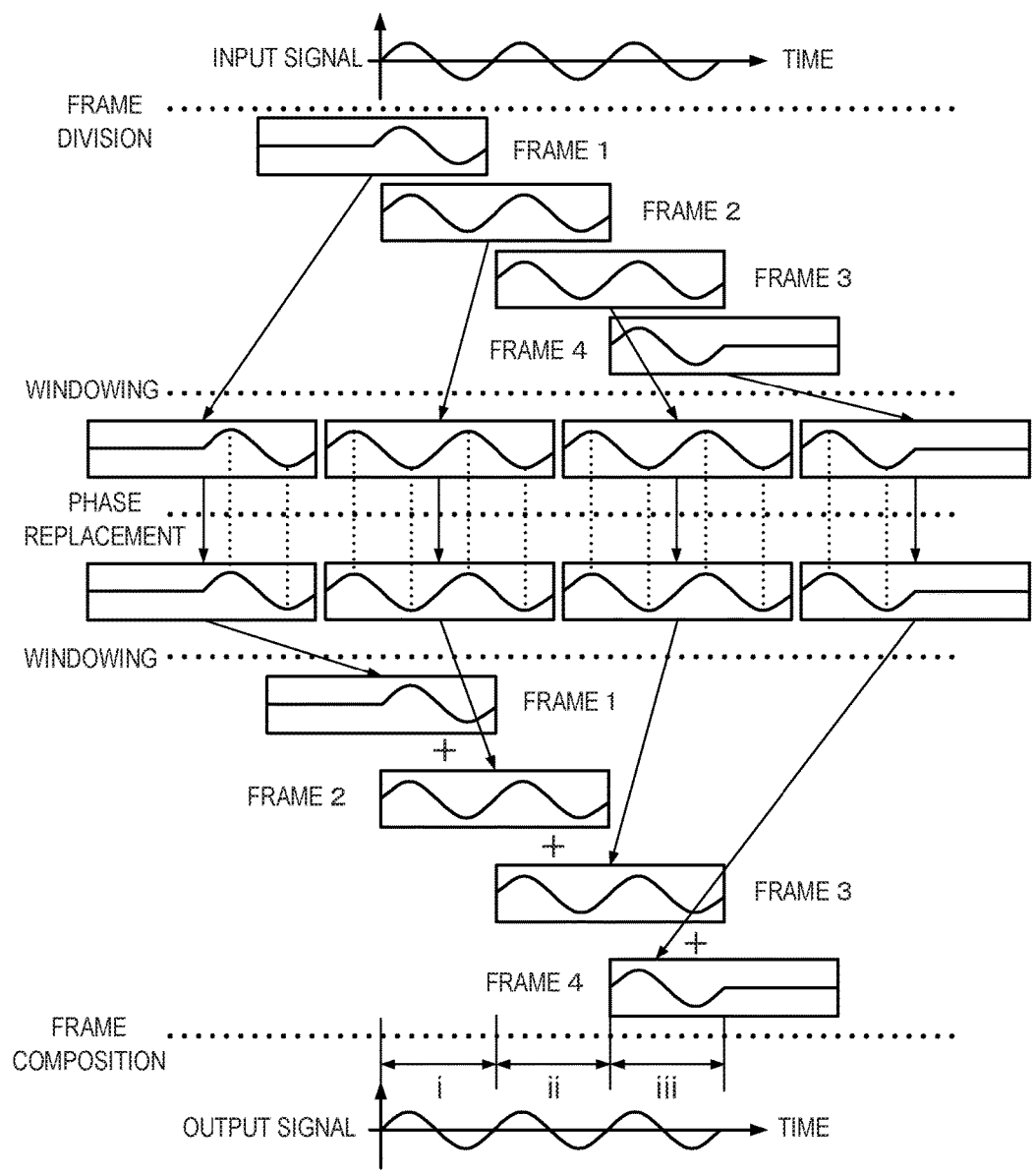
F I G. 6

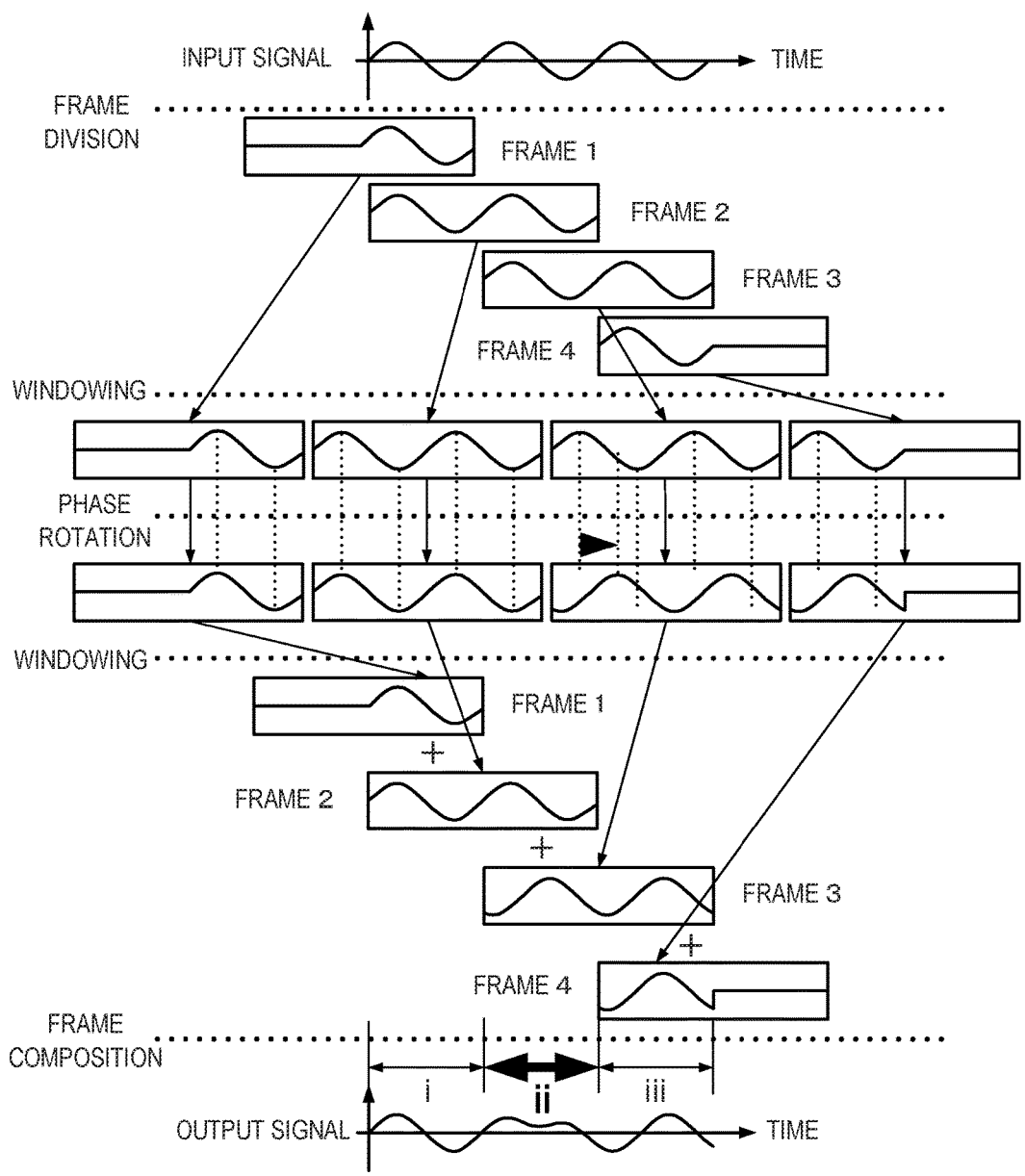
F I G. 7

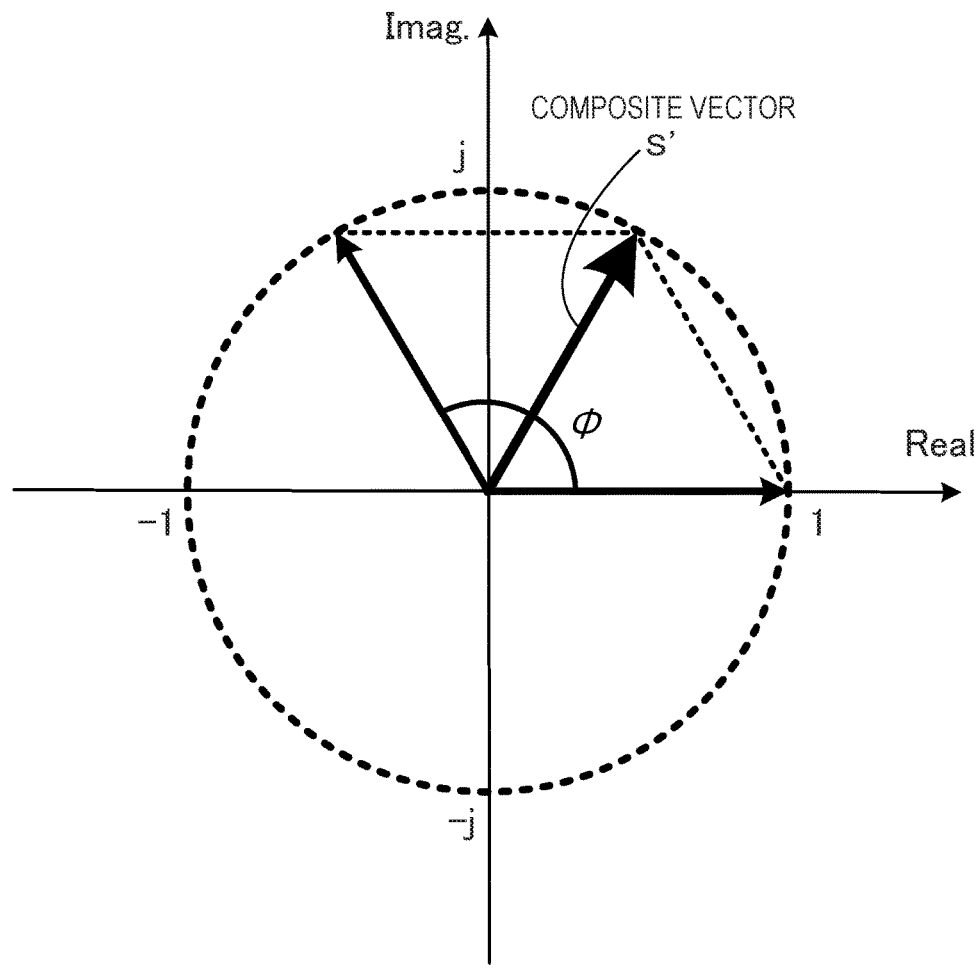
F I G. 10

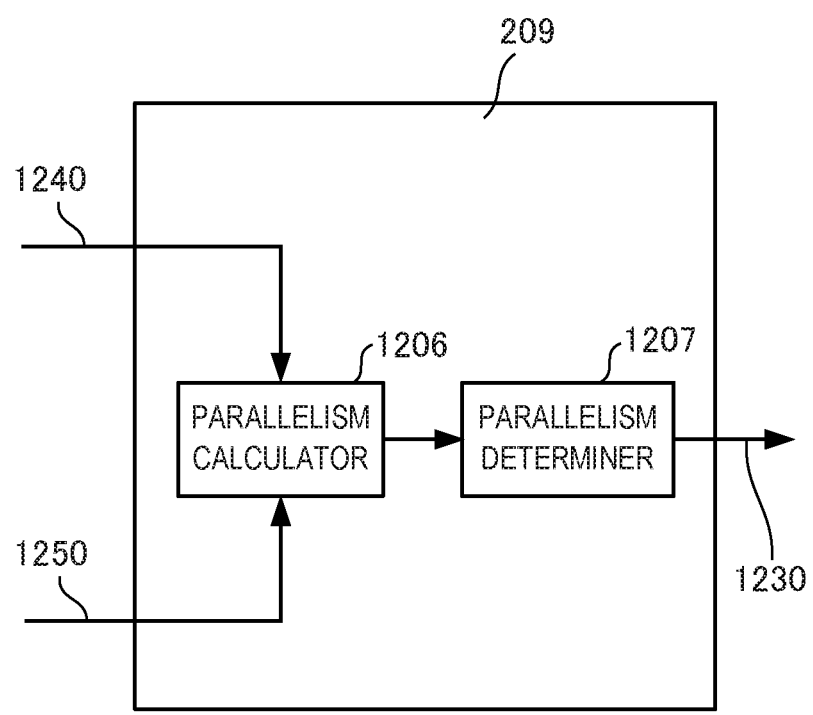
F I G. 12

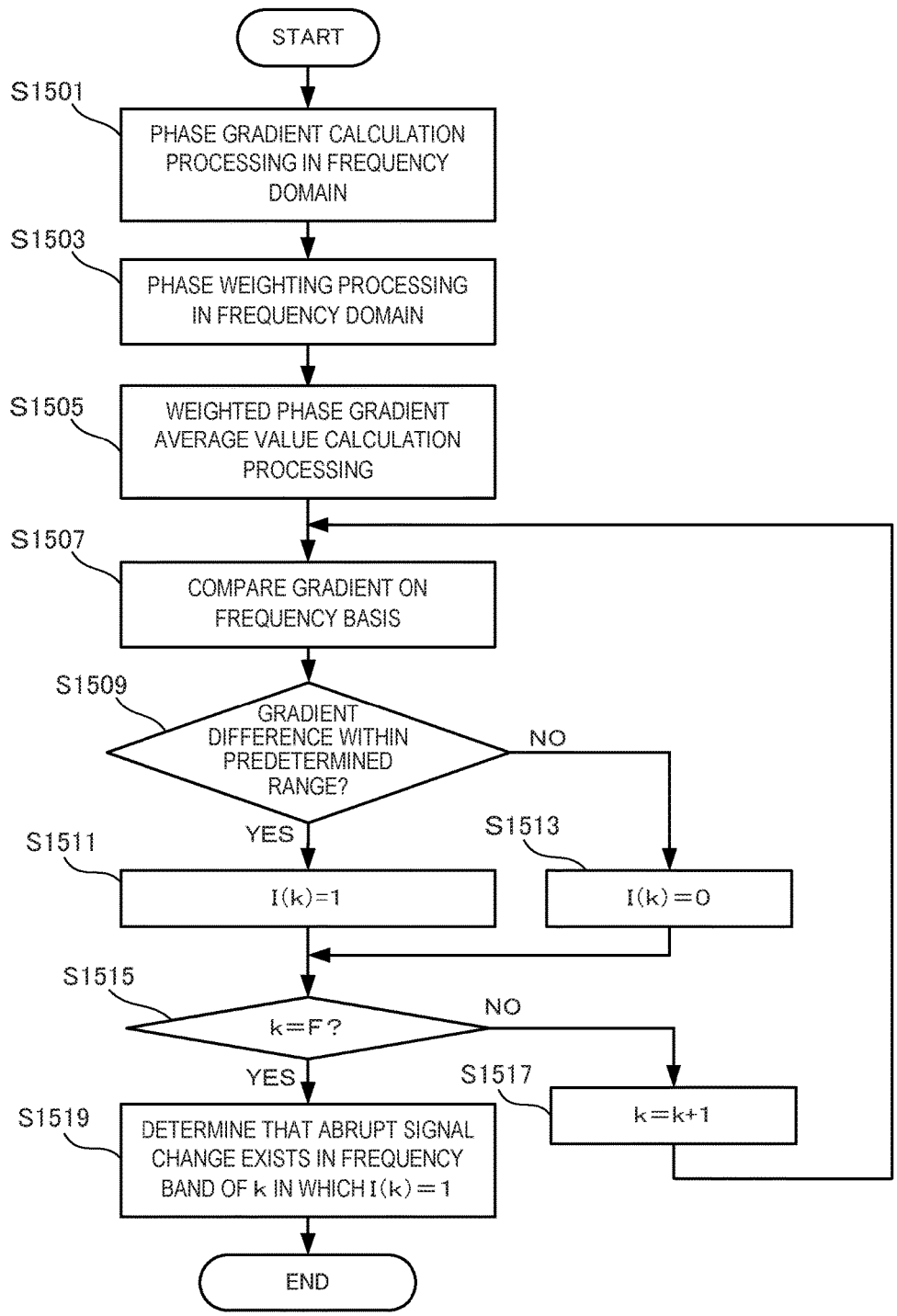
F I G. 15A

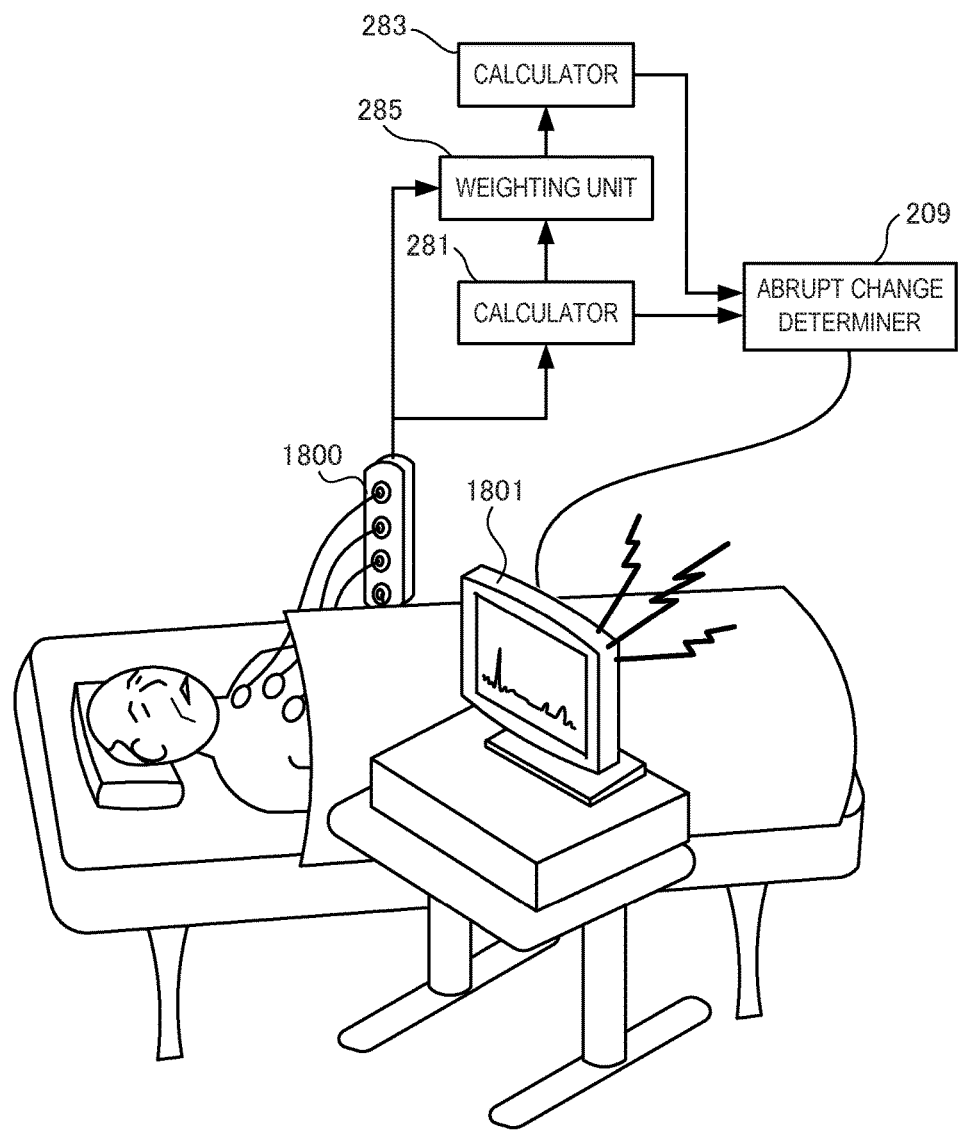
F I G. 18

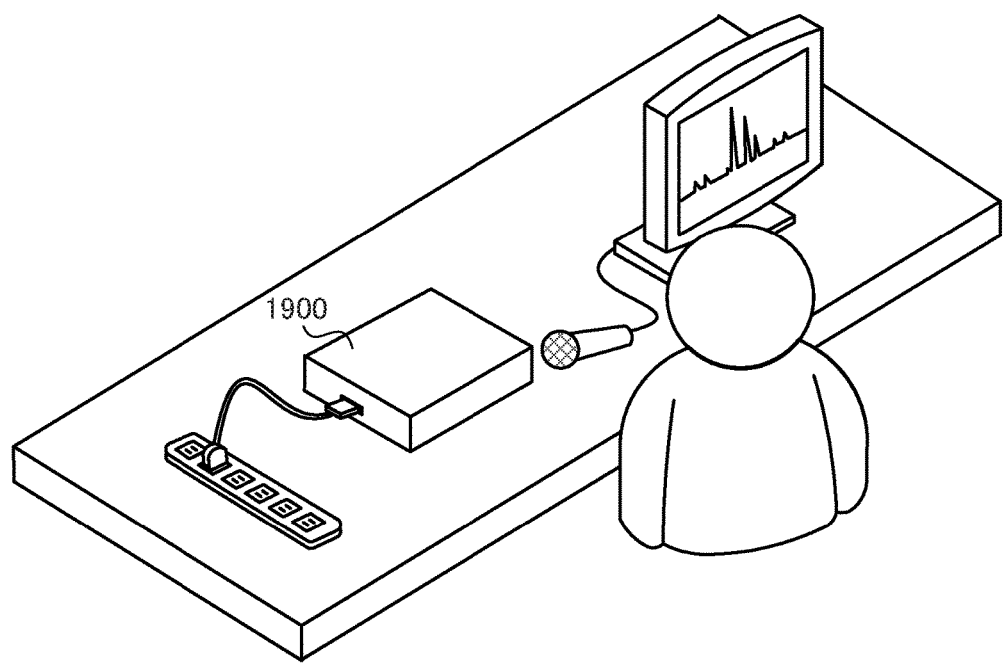
F I G. 19

SIGNAL PROCESSING APPARATUS, SIGNAL PROCESSING METHOD, AND SIGNAL PROCESSING PROGRAM

CROSS-REFERENCE TO RELATED PATENT APPLICATIONS

This application is a National Stage Entry of International Application No. PCT/JP2014/065857, filed Jun. 16, 2014, which claims priority from Japanese Patent Application No. 2013-180735, filed Aug. 30, 2013. The entire contents of the above-referenced applications are expressly incorporated herein by reference.

TECHNICAL FIELD

The present invention relates to a technique of detecting a change in a signal.

BACKGROUND ART

In the above technical field, patent literature 1 describes detection of an abrupt frequency change by measuring a fluctuation in a phase in the time direction. Patent literature 2 describes, in paragraph 0031, that "a phase linearizer 25 corrects a hop in a phase signal θ input from a polar coordinate converter 24 by linearization and outputs a resultant phase signal θ' to a phase detector 26". Non-patent literature 9 describes detecting an abrupt signal change using the frequency-direction linearity of a phase.

CITATION LIST

Patent Literature

Patent literature 1: Japanese Patent Laid-Open No. 2011-254122
Patent literature 2: Japanese Patent Laid-Open No. 2011-199808

Non-Patent Literature

Non-patent literature 1: M. Kato, A. Sugiyama, and M. Serizawa, "Noise suppression with high speech quality based on weighted noise estimation and MMSE STSA", IEICE Trans. Fundamentals (Japanese Edition), vol. J87-A, no. 7, pp. 851-860, July 2004.
Non-patent literature 2: R. Martin, "Spectral subtraction based on minimum statistics", EUSPICO-94, pp. 1182-1185, September 1994.
Non-patent literature 3: "1.5-Mbit/s encoding of video signal and additional audio signal for digital storage media—section 3, audio", JIS X 4323, p. 99, November 1996.
Non-patent literature 4: A. D. Cheveigne and H. Kawahara, "YIN, a fundamental frequency estimator for speech and music", J. Acoustic Soc. Amer., vol. 111, no. 4, pp. 1917-1930, April 2002.
Non-patent literature 5: J. L. Flanagan et al., "Speech Coding", IEEE Transactions on Communications, Vol. 27, no. 4, April 1979.
Non-patent literature 6: A. Subramanya et al., "Automatic removal of typed keystrokes from speech signals", IEEE Signal Processing Letters, Vol. 14, No. 5, pp. 363-366, May 2007.
Non-patent literature 7: J. Murphy et al., "Joint Baysian removal of impulse and background noise", IEEE Proceedings of ICASSP, pp. 261-264, May 2011.
Non-patent literature 8: R. Talmon et al., "Transient noise reduction using nonlocal diffusion filters", IEEE Transactions on Audio, Speech, and Language Processing, Vol. 19, No. 6, pp. 1584-1599, June 2011.
Non-patent literature 9: A. Sugiyama et al., "Impact-noise suppression with phase-based detection," Proc. of IEICE General Conference, pp. 73, March 2013.

SUMMARY OF THE INVENTION

Technical Problem

However, in patent literature 1 out of the techniques describes in the above-described related arts, an abrupt change in a "frequency" is detected. In patent literature 2, equalization processing is performed using a phase gradient. In non-patent literature 9, a method of detecting an ideal pulse is used. That is, the techniques described in these literatures cannot effectively detect an abrupt change in a signal.

The present invention enables to provide a technique of solving the above-described problems.

Solution to Problem

One aspect of the present invention provides a signal processing apparatus comprising:
a converter that converts an input signal into a phase component signal in a frequency domain;
a first calculator that calculates a phase gradient of the phase component signal for each of a plurality of frequencies as a first phase gradient;
a weighting unit that weights the first phase gradient with an amplitude or a power of the input signal, thereby calculating a weighted first phase gradient;
a second calculator that calculates a second phase gradient based on the weighted first phase gradient; and
a determiner that determines presence of an abrupt change in the input signal based on the first phase gradient and the second phase gradient.

Another aspect of the present invention provides a signal processing method comprising:
converting an input signal into a phase component signal in a frequency domain;
calculating a first phase gradient for each of a plurality of frequencies of the phase component signal;
weighting the first phase gradient with an amplitude or a power of the input signal, thereby calculating a weighted first phase gradient;
calculating a second phase gradient using the weighted first phase gradients; and
determining presence of an abrupt change in the input signal based on the first phase gradients and the second phase gradient.

Still other aspect of the present invention provides a signal processing program for causing a computer to execute a method comprising:
converting an input signal into a phase component signal in a frequency domain;
calculating a first phase gradient for each of a plurality of frequencies of the phase component signal;
weighting the first phase gradient by one of an amplitude and a power of the frequency, thereby calculating a weighted first phase gradient;
calculating a second phase gradient using the weighted first phase gradients; and determining presence of an abrupt change in the input signal based on the first phase gradients and the second phase gradient.

Advantageous Effects of Invention

According to the present invention, it is possible to effectively detect an abrupt change in a signal, in particular, an abrupt change different from an ideal pulse.

BRIEF DESCRIPTION OF THE DRAWINGS

FIG. 6 is a view for explaining the operation of the phase controller according to the second embodiment of the present invention;

FIG. 7 is a view for explaining the operation of the phase controller according to the second embodiment of the present invention;

FIG. 10 is a view for explaining the operation of the phase controller according to the second embodiment of the present invention;

FIG. 12 is a block diagram for explaining the arrangement of a calculator and an abrupt change determiner according to the second embodiment of the present invention;

FIG. 15A is a flowchart for explaining the procedure of processing of the noise suppression apparatus according to the second embodiment of the present invention;

FIG. 18 is a view for explaining an application example according to the fourth embodiment of the present invention;

FIG. 19 is a view for explaining an application example according to the fourth embodiment of the present invention.

DESCRIPTION OF THE EMBODIMENTS

Preferred embodiments of the present invention will now be described in detail with reference to the drawings. It should be noted that the relative arrangement of the components, the numerical expressions and numerical values set forth in these embodiments do not limit the scope of the present invention unless it is specifically stated otherwise. Note that "speech signal" in the following explanation indicates a direct electrical change that occurs in accordance with the influence of speech or another sound. The speech signal transmits speech or another sound and is not limited to speech.

First Embodiment

Figure 1:
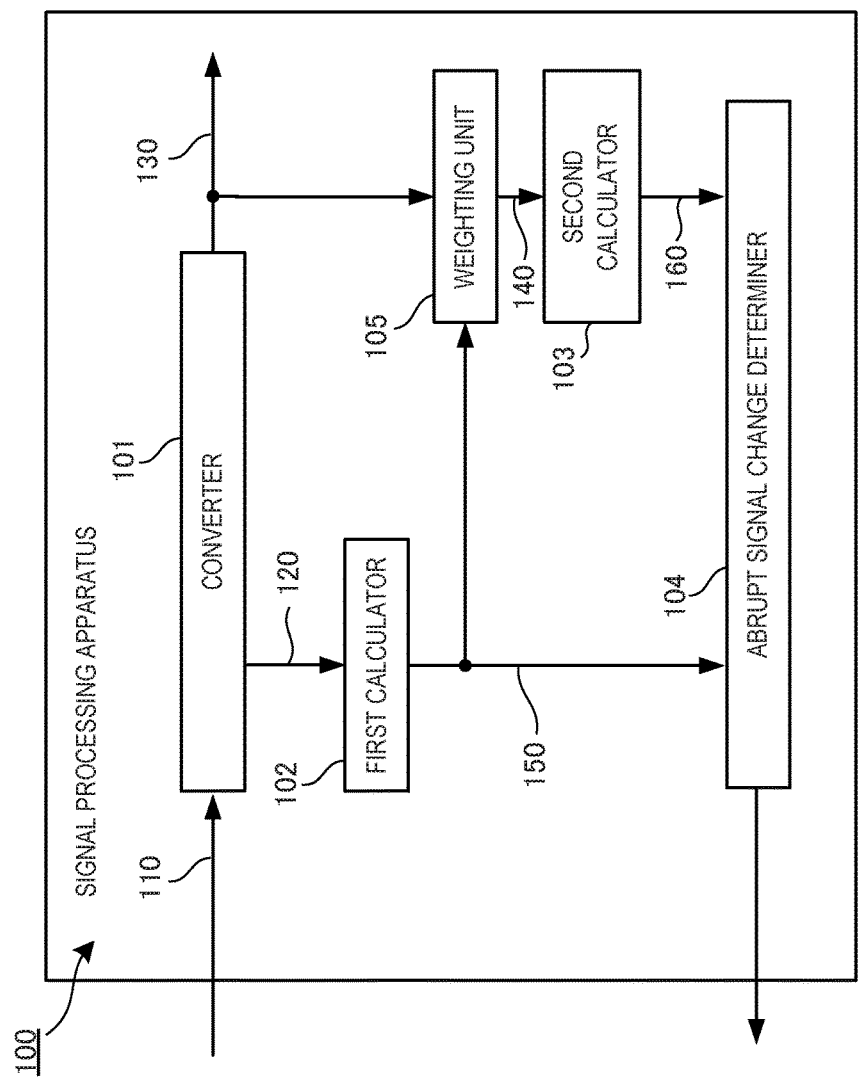
FIG. 1 is a block diagram showing the arrangement of a signal processing apparatus according to the first embodiment of the present invention.

A signal processing apparatus 100 according to the first embodiment of the present invention will be described with reference to FIG. 1. The signal processing apparatus 100 is an apparatus for detecting an abrupt input signal change. The signal processing apparatus 100 includes a converter 101, a first calculator 102, a second calculator 103, a weighting unit 105, and an abrupt signal change determiner 104, as shown in FIG. 1.

The converter 101 converts an input signal 110 into a phase component signal 120 and an amplitude component signal 130 in a frequency domain. The first calculator 102 calculates a phase gradient at each of a plurality of frequencies of the phase component signal 120 as a first gradient 150. The first gradient may be calculated by differentiation using the frequency of the phase or by another method. The weighting unit 105 weights the first gradient 150 by the amplitude component signal 130, thereby calculating a weighted first gradient 140. For example, as the amplitude component signal 130, the weighting unit 105 may use an absolute amplitude value or a power of the amplitude. For example, weighting by the weighting unit 105 may be obtained as a simple product of two values or may be implemented in a form expressed as a function or polynomial. That is, the form of the function or polynomial is not particularly limited as long as the magnitude of the amplitude component signal 130 is reflected on the first gradient in some kind of form. The weighting operation aims at preprocessing the first phase gradient of the frequency with a large amplitude so as to attain greater contribution in the operation of the second calculator. The second calculator 103 calculates a second gradient 160 using the weighted first gradient 140. As the second gradient 160, the average of weighted first gradients can be used. As the second gradient 160, the average of weighted first gradients may be obtained, and the average of a group excluding gradients largely different from the average, that is, a partial average of the weighted first gradients may be used. Since the phase gradient of an abrupt signal change portion to the frequency is ideally constant independently of the frequency, a value largely different from the average gradient is unreliable. For example, the signal includes noise or interfering signal other than a signal constructing an abrupt signal change at a high possibility. Hence, when a partial average excluding values largely different from the average is calculated as the second gradient, an accurate average value, that is, second gradient can be obtained.

When obtaining the average of the weighted first gradients as the second gradient, the second calculator 103 can use a partial average of the weighted first gradients at frequencies in which speech is not dominant. To do this, the second calculator 103 determines, for each frequency, whether or not speech is dominant using the amplitude component signal 130. Whether or not speech is dominant can be evaluated by applying various methods. A frequency having a large amplitude or power can be determined to be a frequency in which speech is dominant. A formant frequency representing speech, in particular, a feature of speech is known to have an amplitude or power much larger than those of other frequencies. Alternatively, an average amplitude or average power of a plurality of frequencies may be obtained, and a frequency having an amplitude or power larger than the value may be determined to be a frequency in which speech is dominant. Determination of a frequency in which speech is dominant may be done only for a low frequency band in which speech exists at a high possibility. When a partial average is used, the adverse effect of speech other than a signal component to detect an abrupt signal change on the averaging result can be reduced, and an accurate average value, that is, second gradient can be obtained.

When obtaining the average of the weighted first gradients as the second gradient, the second calculator 103 may use the average of weighted first gradients at frequencies each having an amplitude or power much larger than the estimated amplitude or power of background noise, that is, a partial average of the first gradients. This is because the amplitude or power of an abrupt signal change portion to be detected is often much larger than the amplitude or power of background noise. To estimate the amplitude or power of the background noise, various methods such as the methods described in non-patent literatures 1 and 2 are usable. If a signal other than the detection target signal and the background noise exists, the signal can similarly be estimated and handled like the background noise. If the amplitude characteristic or power characteristic of the signal other than the detection target signal and the background noise is known in advance, this information may be used. When a partial average is used, the adverse effect of a signal component other than a signal component to detect an abrupt signal change on the averaging result can be reduced, and an accurate average value, that is, second gradient can be obtained.

Alternatively, when obtaining the average of the weighted first gradients as the second gradient, the second calculator 103 may use the average of first gradients at frequencies in which speech is not dominant and which have an amplitude or power much larger than the estimated amplitude or power of background noise. This is an example in which the limiting conditions in the two calculations described above are simultaneously applied.

The abrupt signal change determiner 104 determines an abrupt change in the input signal based on the first gradient 150 calculated by the first calculator 102 and the second gradient 160 calculated by the second calculator 103. A frequency whose difference between the first gradient and the second gradient is small is determined to include an abrupt change in the signal at a high probability.

With the above-described arrangement, it is possible to effectively detect an abrupt change in the input signal, in particular, an abrupt change different from an ideal pulse using the level of matching between the first gradient and the second gradient of the phase component signal in the frequency domain.

Second Embodiment

Overall Arrangement

A noise suppression apparatus according to the second embodiment of the present invention will be described with reference to FIGS. 2 to 11. The noise suppression apparatus according to this embodiment is applicable to suppress noise in, for example, a digital camera, a notebook personal computer, a mobile phone, a keyboard, a game machine controller, and the push buttons of a mobile phone. That is, the target speech signal of speech, music, environmental sound, or the like can be enhanced relative to a signal (noise or interfering signal) superimposed on it. However, the present invention is not limited to this, and the noise suppression apparatus is applicable to a signal processing apparatus of any type required to do abrupt signal change detection from an input signal. Note that in this embodiment, a noise suppression apparatus that detects and suppresses an impulsive sound as an example of an abrupt change in a signal will be described. The noise suppression apparatus according to this embodiment appropriately suppresses an impulsive sound generated by, for example, a button operation in a mode to perform an operation such as button pressing near a microphone. Simply speaking, a time domain signal including an impulsive sound is converted into a frequency domain signal, and a gradient of a phase component in the frequency space is calculated. In addition, the theoretical value of a gradient, that is, a correct gradient is estimated using a value calculated by weighting the obtained gradient by the amplitude. Then, the presence of an impulsive sound is determined in accordance with the level of matching between the two types of phases (the gradient and the theoretical value of the gradient).

Figure 2:
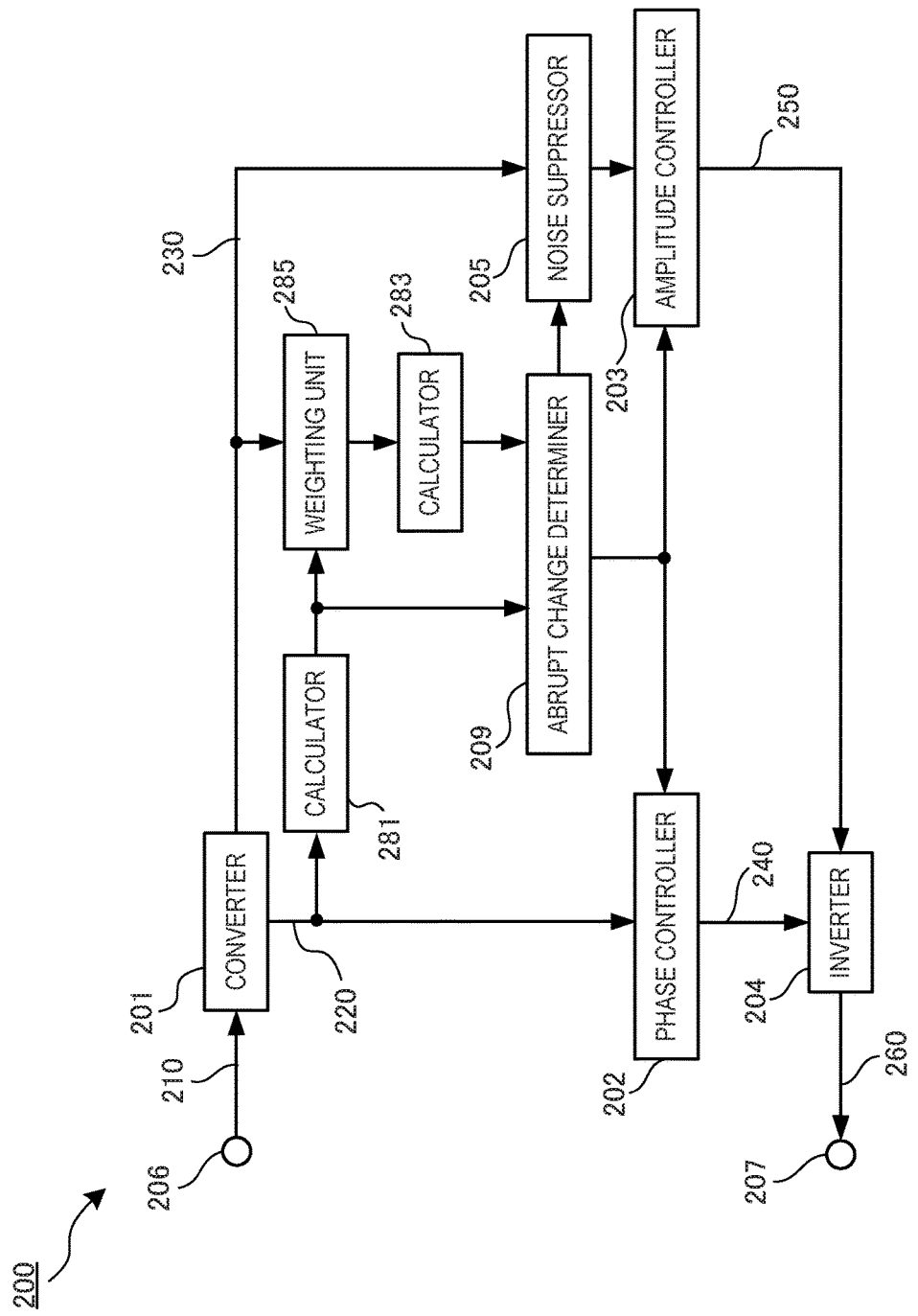
FIG. 2 is a block diagram showing the arrangement of a noise suppression apparatus according to the second embodiment of the present invention.

FIG. 2 is a block diagram showing the overall arrangement of a noise suppression apparatus 200. A noisy signal (signal including both a desired signal and noise) is supplied to an input terminal 206 as a series of sample values. The noisy signal supplied to the input terminal 206 undergoes transform such as Fourier transform in a converter 201 and is divided into a plurality of frequency components. The plurality of frequency components are independently processed on a frequency basis. The description will be continued here concerning a specific frequency component of interest. Out of the frequency component, an amplitude spectrum (amplitude component) 230 is supplied to a noise suppressor 205, and a phase spectrum (phase component) 220 is supplied to a phase controller 202 and a calculator 281. Note that the converter 201 supplies the noisy signal amplitude spectrum 230 to the noise suppressor 205 here. However, the present invention is not limited to this, and a power spectrum corresponding to the square of the amplitude spectrum may be supplied to the noise suppressor 205.

The noise suppressor 205 estimates noise using the noisy signal amplitude spectrum 230 supplied from the converter 201, thereby generating an estimated noise spectrum. In addition, the noise suppressor 205 suppresses the noise using the generated estimated noise spectrum and the noisy signal amplitude spectrum 230 supplied from the converter 201, and transmits an enhanced signal amplitude spectrum as a noise suppression result to an amplitude controller 203. The noise suppressor 205 also receives a determination result from an abrupt change determiner 209, and changes the degree of noise suppression in accordance with the presence/absence or likelihood of an abrupt change presence in the signal. The noise suppressor 205 may detect a desired signal and protect the desired signal component for each frequency, and may also replace the amplitude with an estimated background sound if an abrupt signal change exists, and the desired signal component is not detected.

The phase controller 202 rotates (shifts) the noisy signal phase spectrum 220 supplied from the converter 201, and supplies it to an inverter 204 as an enhanced signal phase spectrum 240. The phase controller 202 also transmits the phase rotation amount (shift amount) to the amplitude controller 203. The amplitude controller 203 receives the phase rotation amount (shift amount) from the phase controller 202, calculates an amplitude correction amount, corrects the enhanced signal amplitude spectrum in each frequency using the amplitude correction amount, and supplies a corrected amplitude spectrum 250 to the inverter 204. The inverter 204 performs inversion by compositing the enhanced signal phase spectrum 240 supplied from the phase controller 202 and the corrected amplitude spectrum 250 supplied from the amplitude controller 203, and supplies the resultant signal to an output terminal 207 as an enhanced signal.

The calculator 281 differentiates the phase component signal 220 supplied from the converter 201 by a frequency, thereby calculating the gradient (change) of the phase at each frequency. The calculator 281 can also approximate the phase gradient by the frequency by obtaining the phase difference between adjacent frequencies. A weighting unit 285 weights the first gradient by the amplitude component signal 230, thereby calculating a weighted first gradient. As the amplitude component signal 230, an absolute amplitude value or a power of the amplitude may be used. Weighting may be obtained as a simple product of two values or may be implemented in a form expressed as a function or polynomial. That is, the form of the function or polynomial is not particularly limited as long as the magnitude of the amplitude component signal 230 is reflected on the first gradient in some kind of form. The weighting operation aims at preprocessing the first phase gradient of the frequency with a large amplitude so as to attain greater contribution in the operation of the second calculator.

On the other hand, a calculator 283 averages the weighted phase gradients at the frequencies supplied from the weighting unit 285 to calculate the average value, and calculates the averaged weighted phase gradient. The abrupt change determiner 209 compares the phase gradient and the weighted average value provided by the calculators 281 and 283, and based on the similarity between them, determines for each frequency point how likely an abrupt change exists in the signal.

As the similarity of gradients, the absolute difference between the gradient obtained from a time domain signal and the gradient obtained from a frequency domain signal can be used. However, the present invention is not limited to this. The distance between 1 and the value of the ratio of the two values, the distance between 1 and a value obtained by normalizing the sum of two values by the two times of one gradient, or the like is also usable. The presence score based on the similarity can be obtained, for example, in the following way. First, a positive value is determined as a threshold. When the absolute difference is larger than the threshold, the score is 1. When the absolute difference equals 0, the score is 0. A general presence score is defined as a function of the absolute difference. The simplest function is a straight line. A presence score is a value proportional to the absolute difference. The slope and y-intercept (the function value when the absolute difference is 0) of the line are determined so as to meet a boundary condition when the above-described absolute difference equals 0 or 1. As the function, an arbitrary linear or nonlinear function or polynomial may also be used.

<<Arrangement of Converter>>

Figure 3:
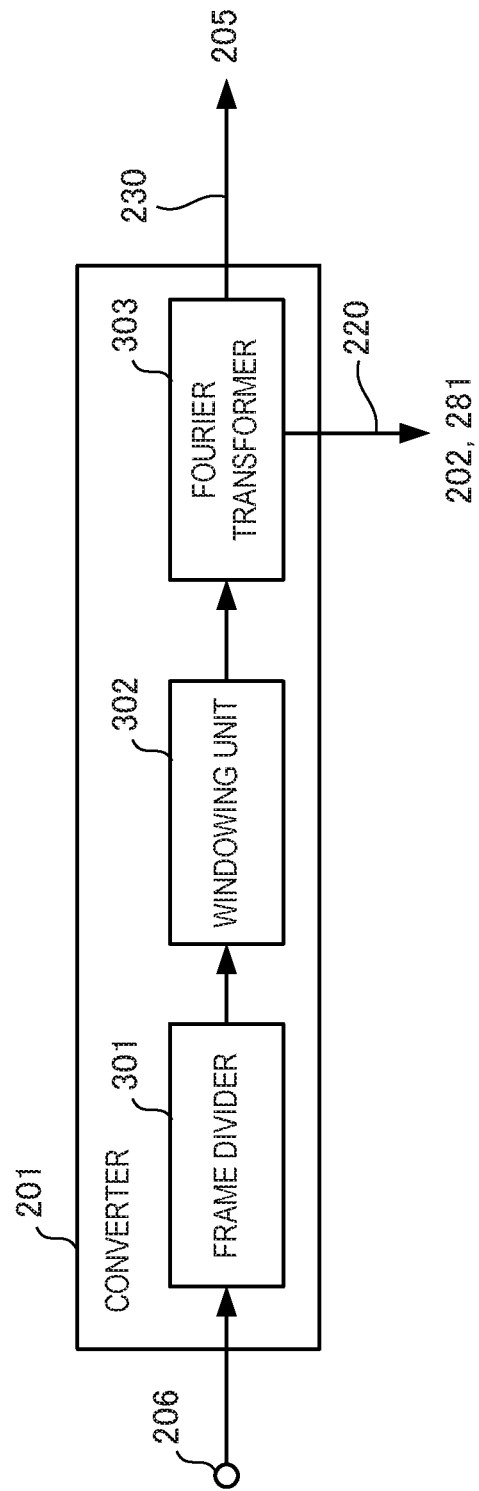
FIG. 3 is a block diagram showing the arrangement of a converter according to the second embodiment of the present invention.

FIG. 3 is a block diagram showing the arrangement of the converter 201. As shown in FIG. 3, the converter 201 includes a frame divider 301, a windowing unit 302, and a Fourier transformer 303. A noisy signal sample is supplied to the frame divider 301 and divided into frames on the basis of K/2 samples, where K is an even number. A noisy signal sample 270 divided into frames is supplied to the windowing unit 302. The windowing unit 302 multiplies the noisy signal sample 270 by a window function w(t). The signal obtained by windowing an nth frame input signal yn(t) (t=0, 1, ..., K/2−1) by w(t) is given by $$\bar{y}_n(t) = w(t) y_n(t) \qquad (1)$$

Two successive frames may partially be overlaid (overlapped) and windowed. Assume that the overlap length is 50% the frame length. For t=0, 1, ..., K/2−1, the windowing unit 302 outputs the left-hand sides of $$\left. \begin{array}{l} \bar{y}_n(t) = w(t) y_{n-1}(t + K/2) \\ \bar{y}_n(t + K/2) = w(t + K/2) y_n(t) \end{array} \right\} \qquad (2)$$

A symmetric window function is used for a real signal. The window function is designed to make the input signal and the output signal match with each other except a calculation error when the output of the converter 201 is directly supplied to the inverter 204. This means $w^2(t) + w^2(t+K/2) = 1$.

The description will be continued below assuming an example in which windowing is performed for two successive frames that overlap 50%. As w(t), the windowing unit can use, for example, a Hanning window given by $$w(t) = \begin{cases} 0.5 + 0.5 \cos\left(\dfrac{\pi(t - K/2)}{K/2}\right), & 0 \le t < K \\ 0, & \text{otherwise} \end{cases} \qquad (3)$$

Various window functions such as a Hamming window and a triangle window are also known. The windowed output is supplied to the Fourier transformer 303 and transformed into a noisy signal spectrum Yn(k). The noisy signal spectrum Yn(k) is separated into the phase and the amplitude. The noisy signal phase spectrum argYn(k) is supplied to the phase controller 202 and the calculator 281, whereas the noisy signal amplitude spectrum |Yn(k)| is supplied to the noise suppressor 205. As already described, a power spectrum may be used in place of the amplitude spectrum.

<<Arrangement of Inverter>>

Figure 4:
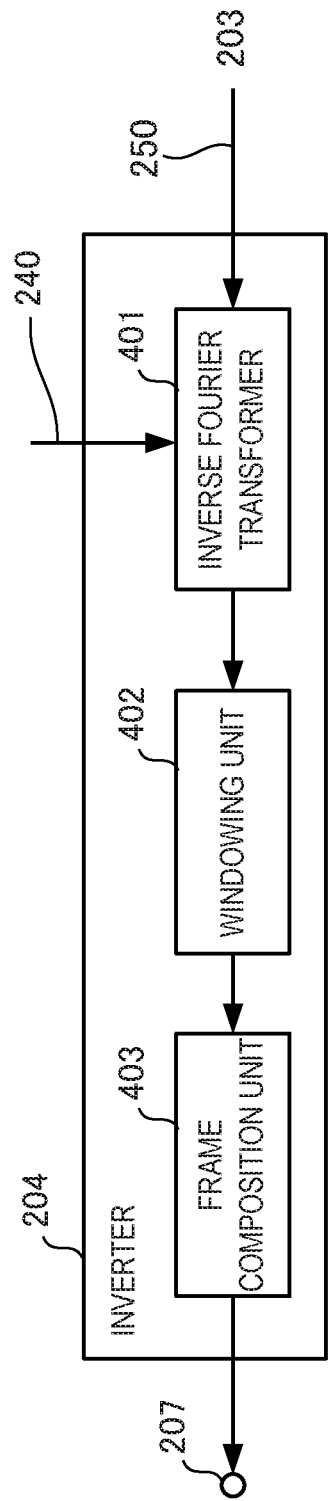
FIG. 4 is a block diagram showing the arrangement of an inverter according to the second embodiment of the present invention.

FIG. 4 is a block diagram showing the arrangement of the inverter 204. As shown in FIG. 4, the inverter 204 includes an inverse Fourier transformer 401, a windowing unit 402, and a frame composition unit 403. The inverse Fourier transformer 401 multiplies the enhanced signal amplitude spectrum 250 supplied from the amplitude controller 203 by the enhanced signal phase spectrum 240 (argXn(k)) supplied from the phase controller 202 to obtain an enhanced signal (the left-hand side of equation (4)).

$$\overline{X}_n(k) = |\overline{X}_n(k)| \cdot argX_n(k) \qquad (4)$$

Inverse Fourier transform is performed for the obtained enhanced signal. The signal is supplied to the windowing unit 402 as a series of time domain sample values xn(t) (t=0, 1, . . . , K−1) in which one frame includes K samples, and multiplied by the window function w(t). A signal obtained by windowing an nth frame input signal xn(t) (t=0, 1, . . . , K/2−1) by w(t) is given by the left-hand side of $$\overline{x}_n(t) = w(t)x_n \qquad (5)$$

Two successive frames may partially be overlaid (overlapped) and windowed. Assume that the overlap length is 50% the frame length. For t=0, 1, . . . , K/2−1, the windowing unit 402 outputs the left-hand sides of $$\overline{x}_n(t) = w(t)x_{n-1}(t + K/2) \\ \overline{x}_n(t + K/2) = w(t + K/2)x_n(t) \qquad (6)$$

and transmits them to the frame composition unit 403.

The frame composition unit 403 extracts the outputs of two adjacent frames from the windowing unit 402 on the basis of K/2 samples, overlays them, and obtains an output signal (left-hand sides of equation (7)) for t=0, 1, . . . , K−1 by $$\hat{x}_n(t) = \overline{x}_{n-1}(t + K/2) + \overline{x}_n(t) \qquad (7)$$

An obtained enhanced signal 260 is transmitted from the frame composition unit 403 to the output terminal 207.

Note that the conversion in the converter and the inverter in FIGS. 3 and 4 has been described as Fourier transform. However, any other transform such as Hadamard transform, Haar transform, or Wavelet transform may be used in place of the Fourier transform. Haar transform does not need multiplication and can reduce the area of an LSI chip. Wavelet transform can change the time resolution depending on the frequency and is therefore expected to improve the noise suppression effect.

The noise suppressor 205 may perform actual suppression after a plurality of frequency components obtained by the converter 201 are integrated. The number of frequency components after integration is smaller than the number of frequency components before integration. More specifically, a common suppression level is obtained for integrated frequency components obtained by integrating the frequency components. The suppression level is commonly used for individual frequency components belonging to the same integrated frequency component. At this time, high sound quality can be achieved by integrating more frequency components from the low frequency range where the discrimination capability of hearing characteristics is high to the high frequency range with a poorer capability. When noise suppression is executed after integrating a plurality of frequency components, the number of frequency components to which noise suppression is applied decreases, and the whole calculation amount can be decreased.

<<Arrangement of Noise Suppressor>>

The noise suppressor 205 estimates noise using the noisy signal amplitude spectrum supplied from the converter 201 and generates an estimated noise spectrum. The noise suppressor 205 then obtains a suppression coefficient using the noisy signal amplitude spectrum from the converter 201 and the generated estimated noise spectrum, multiplies the noisy signal amplitude spectrum by the suppression coefficient, and supplies the resultant spectrum to the amplitude controller 203 as an enhanced signal amplitude spectrum. In addition, the noise suppressor 205 receives an abrupt change determination result (information representing whether an abrupt signal change exists) from the abrupt change determiner 209. If it is determined that an abrupt change exists, a smaller one of the noisy signal amplitude spectrum and the estimated noise spectrum is supplied to the amplitude controller 203 as an enhanced signal amplitude spectrum. At this time, the noise suppressor 205 may detect a desired signal and protect the desired signal component for each frequency.

In addition, upon receiving the presence score of an abrupt change which is information representing how likely an abrupt change exists, or in other words, likelihood that an abrupt signal change exists, from the abrupt change determiner 209, the degree of noise suppression can be changed in accordance with the possibility that an abrupt signal change exists. It is also possible to determine the possibility that an abrupt signal change exists for each frequency component, frequency band (combination of an arbitrary number of continuous frequency components), or frame and perform different signal processing for each frequency component, frequency band, or frame to suppress the abrupt change.

To estimate noise, various estimation methods such as the methods described in non-patent literatures 1 and 2 are usable.

For example, non-patent literature 1 discloses a method of obtaining, as an estimated noise spectrum, the average value of noisy signal amplitude spectra of frames in which no desired signal is generated. In this method, it is necessary to detect the presence of the desired signal. A section where the desired signal exists can be determined by the power of the enhanced signal.

As an ideal operation state, the enhanced signal is the desired signal other than noise. In addition, the level of the desired signal or noise does not largely change between adjacent frames. For these reasons, the enhanced signal level of an immediately preceding frame is used as an index to determine a noise section. If the enhanced signal level of the immediately preceding frame is equal to or smaller than a predetermined value, the current frame is determined as a noise section. A noise spectrum can be estimated by averaging the noisy signal amplitude spectra of frames determined as a noise section.

Non-patent literature 1 also discloses a method of obtaining, as an estimated noise spectrum, the average value of noisy signal amplitude spectra in the early stage in which supply of them has started. In this case, it is necessary to meet a condition that the desired signal is not included immediately after the start of estimation. If the condition is met, the noisy signal amplitude spectrum in the early stage of estimation can be obtained as the estimated noise spectrum.

Non-patent literature 2 discloses a method of obtaining an estimated noise spectrum from the minimum value of the statistical noisy signal amplitude spectrum. In this method, the minimum value of the noisy signal amplitude spectrum within a predetermined time is statistically held, and a noise spectrum is estimated from the minimum value. The minimum value of the noisy signal amplitude spectrum is similar to the shape of a noise spectrum and can therefore be used as the estimated value of the noise spectrum shape. However, the minimum value is smaller than the original noise level. Hence, a spectrum obtained by appropriately amplifying the minimum value is used as an estimated noise spectrum.

The noise suppressor 205 can perform various kinds of suppression. Typical examples are the SS (Spectrum Subtraction) method and an MMSE STSA (Minimum Mean-Square Error Short-Time Spectral Amplitude Estimator) method. In the SS method, the estimated noise spectrum is subtracted from the noisy signal amplitude spectrum supplied from the converter 201. In the MMSE STSA method, a suppression coefficient is calculated using the noisy signal amplitude spectrum supplied from the converter 201 and the generated estimated noise spectrum, and the noisy signal amplitude spectrum is multiplied by the suppression coefficient. The suppression coefficient is decided so as to minimize the mean square power of the enhanced signal.

Additionally, the noise suppressor 205 receives the abrupt change determination result (information representing whether an abrupt signal change exists) from the abrupt change determiner 209, and changes the degree of noise suppression in accordance with the presence/absence or likelihood of an abrupt signal change presence. For example, signal processing can be performed for each frequency component, frequency band, or frame in which an abrupt signal change has occurred to suppress the abrupt change.

If the abrupt change determiner 209 determines that an abrupt change exists, a smaller one of the noisy signal amplitude spectrum and the estimated noise spectrum is supplied to the amplitude controller 203 as an enhanced signal amplitude spectrum. That is, if the noisy signal amplitude spectrum is smaller than the estimated noise spectrum, the noisy signal amplitude spectrum is directly output. Otherwise, the input signal can be replaced with the estimated noise spectrum and output.

It is also possible to, prior to the replacement, detect an important noisy signal amplitude spectrum component and exclude the detected important noisy signal amplitude spectrum component from the component to be replaced with the estimated noise spectrum. As the index of importance when detecting the important noisy signal amplitude spectrum component, the magnitude of the noisy signal amplitude spectrum can be used. A component having a large amplitude is a component of a target signal at a high probability. Holding this component contributes to prevention of a degradation in sound quality of the target signal.

The peak characteristic of the noisy signal amplitude spectrum can also be used as the index of importance. A noisy signal amplitude having a peak, that is, a value larger than peripheral values along the frequency axis is a component of a target signal at a high probability. Holding this component contributes to prevention of a degradation in sound quality of the target signal. In particular, a conspicuous peak, that is, an amplitude value much larger than peripheral amplitude values is important. When this component is reliably protected, sound quality of the target signal can further be increased.

To detect a peak, for example, a pure sound component detection method of non-patent literature 3 or a method disclosed in non-patent literature 4 is usable. A detected peak may be evaluated in accordance with a predetermined condition, and a peak that does not meet the condition may be excluded. For example, there is little possibility that a peak having a value smaller than the estimated noise is the target signal. That is, it is possible to, using the estimated noise as a reference, leave only peaks much larger than the estimated noise and exclude others. Whether a peak is sufficiently large can be determined by comparing it with a constant multiple of the estimated noise. In this way, it is evaluated whether a detected peak meets a predetermined condition, and final peak components are then selected. This can reduce peak detection errors and enhance the effect of suppressing an abrupt signal change portion.

It is also possible to change the signal to be supplied to the amplitude controller 203 in accordance with the likelihood of an abrupt change presence. The result of replacement and the noisy signal amplitude spectrum are mixed in correspondence with the likelihood of an abrupt change presence, and the mixture is output as an enhanced signal amplitude spectrum. The mixing processing is executed by adding a large weight to the replacement result as the likelihood of an abrupt change presence rises.

The noise suppressor 205 may perform suppression in multiple levels such as suppression level 0, suppression level 1, and suppression level 2 in accordance with the presence score of an abrupt signal change. Alternatively, the degree of suppression may continuously be changed in accordance with the determination result (for example, numerical values of 0 to 1) of the abrupt change determiner.

<<Arrangement of Phase Controller and Amplitude Controller>>

Figure 5:
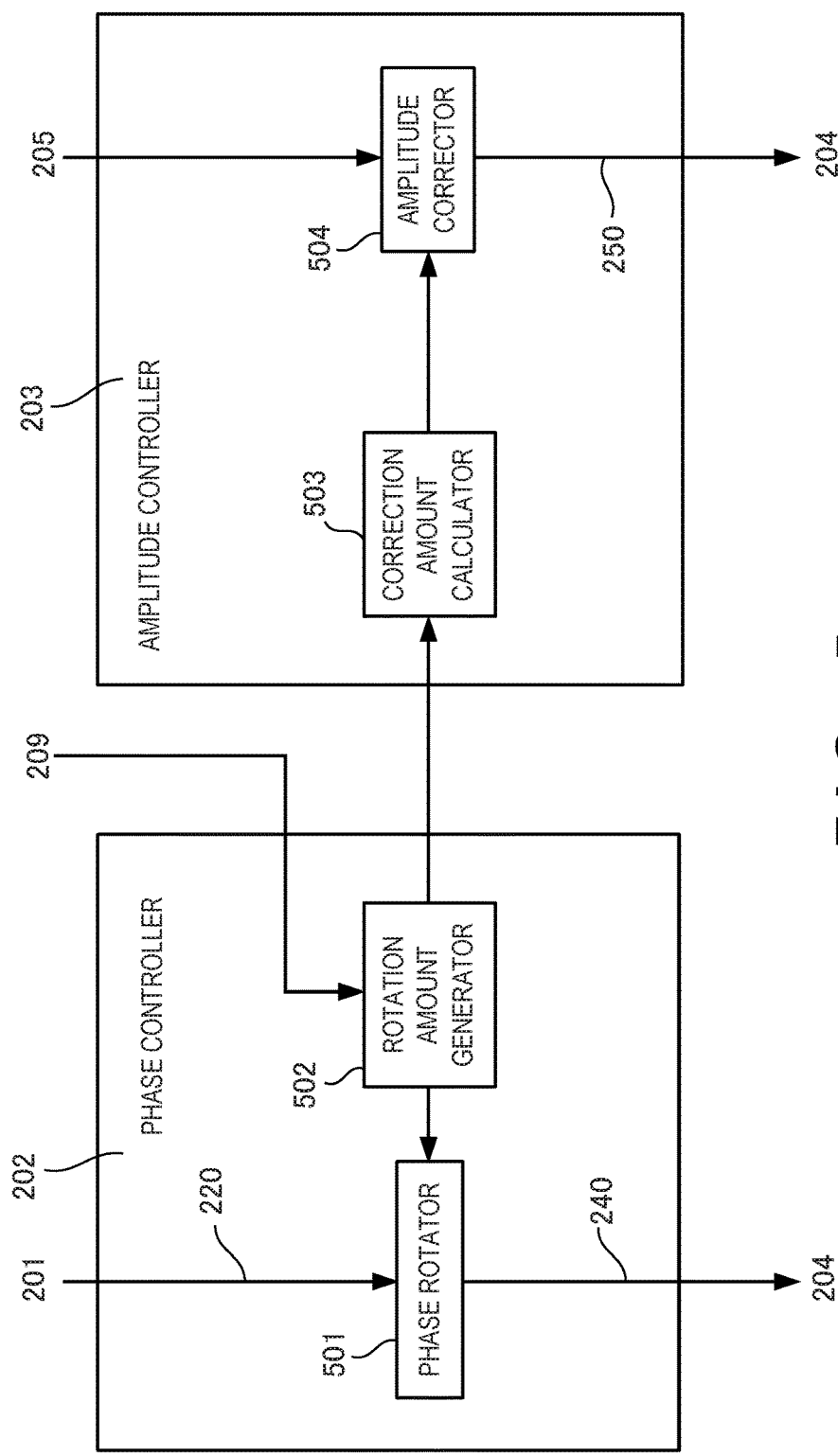
FIG. 5 is a block diagram showing the arrangement of a phase controller and an amplitude controller according to the second embodiment of the present invention.

FIG. 5 is a block diagram showing the arrangement of the phase controller 202 and the amplitude controller 203. As shown in FIG. 5, the phase controller 202 includes a phase rotator 501 and a rotation amount generator 502, and the amplitude controller 203 includes a correction amount calculator 503 and an amplitude corrector 504.

The rotation amount generator 502 generates the rotation amount of the noisy signal phase spectrum for a frequency component determined to "have an abrupt change in the signal" by the abrupt change determiner 209, and supplies the rotation amount to the phase rotator 501 and the correction amount calculator 503. Upon receiving the rotation amount supplied from the rotation amount generator 502, the phase rotator 501 rotates (shifts) the noisy signal phase spectrum 220 supplied from the converter 201 by the supplied rotation amount, and supplies the rotated spectrum to the inverter 204 as the enhanced signal phase spectrum 240.

The correction amount calculator 503 decides the correction coefficient of the amplitude based on the rotation amount supplied from the rotation amount generator 502, and supplies the correction coefficient to the amplitude corrector 504.

The rotation amount generator 502 generates the rotation amount by, for example, a random number. When the noisy signal phase spectrum is rotated for each frequency by a random number, the shape of the noisy signal phase spectrum 220 changes. With the change in the shape, the feature of an abrupt signal change portion such as an impulsive sound can be weakened.

Examples of the random number are a uniform random number whose occurrence probability is uniform and a normal random number whose occurrence probability exhibits a normal distribution. A rotation amount generation method using a uniform random number will be described first. A uniform random number can be generated by a linear congruential method or the like. For example, uniform random numbers generated by the linear congruential method are uniformly distributed within the range of 0 to $(2^M)-1$, where M is an arbitrary integer, and ^ represents a power. Phase rotation amounts $\phi$ need to be distributed within the range of 0 to $2\pi$. To do this, the generated uniform random numbers are converted. The conversion is performed by $$\phi = 2\pi \frac{R}{R_{max}} \quad (8)$$

where R is the uniform random number, and Rmax is the maximum value capable of being generated by the uniform random number. When a uniform random number is generated by the above-described linear congruential method, Rmax=(2^M)−1.

To simplify the calculation, the value R may directly be decided as the rotation amount. As the rotation amount, $2\pi$ represents just one revolution. A case where the phase is rotated by $2\pi$ is equivalent to a case where the phase is not rotated. Hence, a rotation amount $2\pi+\alpha$ is equivalent to a rotation amount $\alpha$. A case where a uniform random number is generated by the linear congruential method has been explained here. Even in a case where a uniform random number is generated by another method, the rotation amount $\phi$ is obtained by equation (8). When and how many times random number generation is to be performed may be decided in accordance with the determination result of the abrupt change determiner 209.

The phase rotator 501 receives the rotation amount from the rotation amount generator 502 and rotates the noisy signal phase spectrum. If the noisy signal phase spectrum is expressed as an angle, it can be rotated by adding the value of the rotation amount $\phi$ to the angle. If the noisy signal phase spectrum is expressed as the normal vector of a complex number, it can be rotated by obtaining the normal vector of the rotation amount $\phi$ and multiplying the noisy signal phase spectrum by the normal vector.

The normal vector of the rotation amount $\phi$ can be obtained by $$\Phi = \cos(\phi) + j\sin(\phi) \quad (9)$$

In equation (9), $\Phi$ is the rotation vector, and j represents sqrt(−1). Note that sqrt is the square root.

A correction coefficient calculation method by the correction amount calculator 503 will be described. First, a decrease in the output level caused by phase rotation will be described first with reference to FIGS. 6 and 7. FIGS. 6 and 7 show signals obtained by processing a noisy signal by the block diagram shown in FIG. 2. The difference between FIGS. 6 and 7 is the presence/absence of phase rotation. FIG. 6 shows a signal in a case where phase rotation is not performed, and FIG. 7 shows a signal in a case where phase rotation is performed from frame 3.

A signal in a case where phase rotation is not performed will be described with reference to FIG. 6. A noisy signal is illustrated in the uppermost portion of FIG. 6. The noisy signal is divided into frames by the frame divider 301. The second signal from above, which is separated by a dotted line, is the signal after frame division. A signal corresponding to four successive frames is illustrated here. The frame overlap ratio is 50%.

The signal divided into frames is windowed by the windowing unit 302. The third signal from above, which is separated by a dotted line, is the signal after windowing. In FIG. 6, to clarify the influence of phase rotation, weighting using a rectangular window is performed.

Next, the Fourier transformer 303 transforms the signal into a signal in a frequency domain. The signal in the frequency domain is not illustrated in FIG. 6. A signal transformed into a time domain by the inverse Fourier transformer 401 of the inverter 204 is shown in the portion under the dotted line of phase rotation. The fourth signal from above, which is separated by a dotted line, is the signal after phase rotation. In FIG. 6, however, the signal does not change from that after windowing because phase rotation is not performed.

Windowing is performed again for an enhanced signal output from the inverse Fourier transformer 401 of the inverter 204. FIG. 6 shows a case where weighting using a rectangular window is performed. The windowed signals are composited by the frame composition unit 403. At this time, times between the frames need to match. Since the overlap ratio is 50%, the frames overlap just in half. If phase rotation is not executed, the input signal and the output signal match, as shown in FIG. 6.

A signal in a case where phase rotation is performed will be described with reference to FIG. 7. FIG. 7 shows a signal in a case where phase rotation is performed from frame 3. The same noisy signal as in FIG. 6 is illustrated in the uppermost portion. The signal after frame division and the signal after windowing are also the same as in FIG. 6.

FIG. 7 illustrates a case where predetermined phase rotation is executed from frame 3. Place focus on the section of a right triangle shown in the portion under the dotted line of phase rotation processing. By phase rotation processing, the signals of frames 3 and 4 shift in the time direction. The signal that has undergone the phase rotation is windowed again, and the frames are composited. At this time, a difference is generated between the signal of frames 2 and that of frame 3 in a section ii where frames 2 and 3 overlap. This makes the output signal level after frame composition small in the section ii. That is, when phase rotation is executed, the output signal level lowers in the section ii in FIG. 7.

Lowering of the output signal level caused by phase rotation can also be explained in vector composition in a frequency domain by replacing addition in the time domain with addition in the frequency domain.

Figure 8:
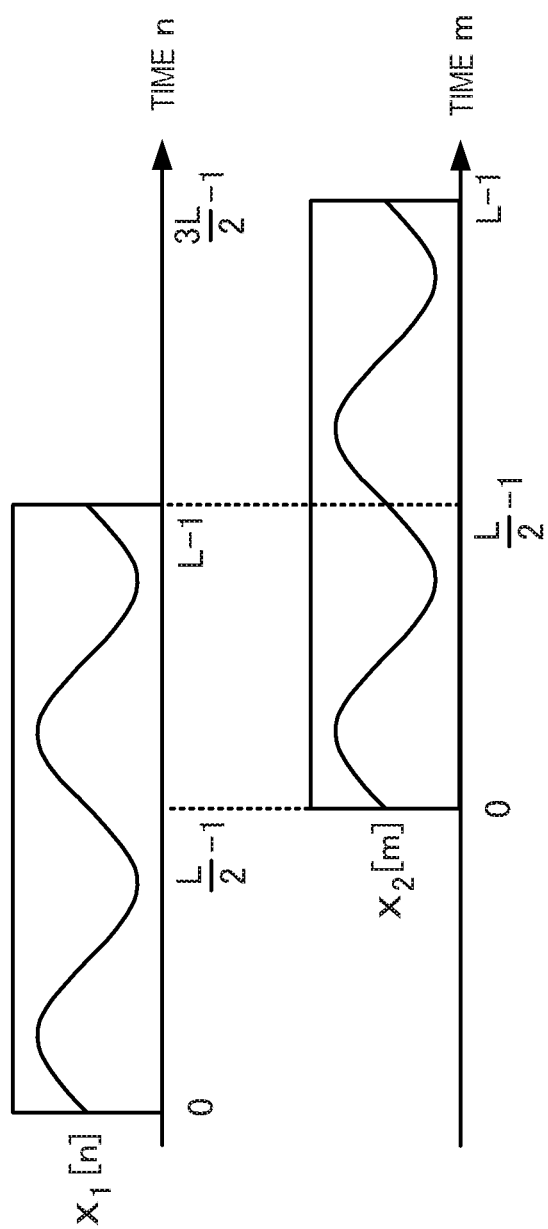
FIG. 8 is a view for explaining the operation of the phase controller according to the second embodiment of the present invention.

FIG. 8 shows the noisy signals of two successive frames after frame division and windowing as x1[n] and x2[m]. Note that the overlap ratio is 50%. Here, n indicates the discrete time of x1, and m indicates the discrete time of x2. When the overlap ratio is 50%, $$m = n + L/2 \quad (10)$$

holds.

In addition, the relationship between x1 and x2 is represented by $$x_2[m] = x_1[n+L/2] \quad (11)$$

The formula of transform from a time domain signal to a frequency domain signal and that of inverse transform will be described. By Fourier transform of a time domain signal x[n], a frequency domain signal X[k] is expressed as $$X[k] = \sum_{n=0}^{L-1} x[n] e^{-j2\pi \frac{n}{L} k} \quad (12)$$

where k is the discrete frequency, and L is the frame length.

When the frequency domain signal X[n] is returned to the time domain signal x[n] by inverse transform, the time domain signal x[n] is expressed as $$x[n] = \frac{1}{L} \sum_{k=0}^{L-1} X[k] e^{j2\pi \frac{n}{L} k} \quad (13)$$

When the time domain signals x1[n] and x2[m] are transformed into frequency domain signals X1[k] and X2[k] based on this equation, they are expressed as $$X_1[k] = \sum_{n=0}^{L-1} x_1[n] e^{-j2\pi \frac{n}{L} k} \qquad (14)$$

$$X_2[k] = \sum_{m=0}^{L-1} x_2[m] e^{-j2\pi \frac{m}{L} k} \qquad (15)$$

When the frequency domain signals X1[k] and X2[k] are returned to the time domain signals x1[n] and x2[m] by inverse transform, respectively, they are expressed, based on equation (13), as $$x_1[n] = \frac{1}{L} \sum_{k=0}^{L-1} X_1[k] e^{j2\pi \frac{n}{L} k} \qquad (16)$$

$$x_2[m] = \frac{1}{L} \sum_{k=0}^{L-1} X_2[k] e^{j2\pi \frac{m}{L} k} \qquad (17)$$

The inverter transforms each frequency domain signal into a time domain signal by Fourier transform. After that, the frame composition unit adds the enhanced signal of the preceding frame and that of the current frame which overlap. For example, when the overlap ratio is 50% as in the illustrated example, the adjacent frames are added in the section of the discrete time m=L/2 to L−1. Consider the addition section m=L/2 to L−1.

When equations (16) and (17) are substituted into time domain addition, the addition is expressed as $$x_1[n] + x_2[m] = \frac{1}{L} \sum_{k=0}^{L-1} X_1[k] e^{j2\pi \frac{n}{L} k} + \frac{1}{L} \sum_{k=0}^{L-1} X_2[k] e^{j2\pi \frac{m}{L} k} \qquad (18)$$

When equations (14) and (15) are further substituted into the frequency domain signals X1[k] and X2[k] in equation (18), the addition is expressed as $$x_1[n] + x_2[m] = \frac{1}{L} \sum_{k=0}^{L-1} X_1[k] e^{j2\pi \frac{n}{L} k} + \frac{1}{L} \sum_{k=0}^{L-1} X_2[k] e^{j2\pi \frac{m}{L} k} \qquad (19)$$

$$= \frac{1}{L} \sum_{k=0}^{L-1} \left( \sum_{n=0}^{L-1} x_1[n] e^{-j2\pi \frac{n}{L} k} \right) e^{j2\pi \frac{n}{L} k} +$$

$$\frac{1}{L} \sum_{k=0}^{L-1} \left( \sum_{m=0}^{L-1} x_2[m] e^{-j2\pi \frac{m}{L} k} \right) e^{j2\pi \frac{m}{L} k}$$

When equations (19) is expanded, the addition is expressed as $$x_1[n] + x_2[m] = \frac{1}{L} \sum_{k=0}^{L-1} \left( \sum_{n=0}^{L-1} x_1[n] e^{-j2\pi \frac{n}{L} k} \right) e^{j2\pi \frac{n}{L} k} + \qquad (20)$$

$$\frac{1}{L} \sum_{k=0}^{L-1} \left( \sum_{m=0}^{L-1} x_2[m] e^{-j2\pi \frac{m}{L} k} \right) e^{j2\pi \frac{m}{L} k}$$

$$= \frac{1}{L} \sum_{k=0}^{L-1} \begin{pmatrix} x_1[0] e^{-j2\pi \frac{0}{L} k} + \\ x_1[1] e^{-j2\pi \frac{1}{L} k} + \ldots + \\ x_1[L-1] e^{-j2\pi \frac{L-1}{L} k} \end{pmatrix} e^{j2\pi \frac{n}{L} k} +$$

$$\frac{1}{L} \sum_{k=0}^{L-1} \begin{pmatrix} x_2[0] e^{-j2\pi \frac{0}{L} k} + \\ x_2[1] e^{-j2\pi \frac{1}{L} k} + \ldots + \\ x_2[L-1] e^{-j2\pi \frac{L-1}{L} k} \end{pmatrix} e^{j2\pi \frac{m}{L} k}$$

$$= \frac{1}{L} \left\{ \begin{array}{l} x_1[0] \sum_{k=0}^{L-1} e^{j\frac{2\pi}{L}(n-0)k} + \\ x_1[1] \sum_{k=0}^{L-1} e^{j\frac{2\pi}{L}(n-1)k} + \ldots + \\ x_1[L-1] \sum_{k=0}^{L-1} e^{j\frac{2\pi}{L}(n-L-1)k} \end{array} \right\} +$$

$$\frac{1}{L} \left\{ \begin{array}{l} x_2[0] \sum_{k=0}^{L-1} e^{j\frac{2\pi}{L}(m-0)k} + \\ x_2[1] \sum_{k=0}^{L-1} e^{j\frac{2\pi}{L}(m-1)k} + \ldots + \\ x_2[L-1] \sum_{k=0}^{L-1} e^{j\frac{2\pi}{L}(m-L-1)k} \end{array} \right\}$$

Consider the sum operation included in each term of equation (20). When an arbitrary integer g is introduced, $$\sum_{k=0}^{L-1} e^{j\frac{2\pi}{L} gk} \qquad (21)$$

holds.

The inverse Fourier transformation of a delta function δ[g] is given by $$\delta[g] = \frac{1}{L} \sum_{k=0}^{L-1} e^{j\frac{2\pi}{L} gk} \qquad (22)$$

The delta function δ[g] is represented by $$\delta[g] = \begin{cases} 1 & g=0 \\ 0 & g \neq 0 \end{cases} \qquad (23)$$

Based on equation (22), expression (21) can be rewritten as $$\sum_{k=0}^{L-1} e^{j\frac{2\pi}{L}gk} = L \cdot \delta[g] \tag{24}$$

From the relation of equation (24), equation (20) is represented by $$x_1[n] + x_2[m] = \frac{1}{L}\left\{\begin{array}{c} L \cdot x_1[0]\delta[0] + L \cdot x_1[1]\delta[n-1] + \ldots + \\ L \cdot x_1[L-1]\delta[n-L+1] \end{array}\right\} + \frac{1}{L}\left\{\begin{array}{c} L \cdot x_2[0]\delta[0] + L \cdot x_2[1]\delta[m-1] + \ldots + \\ L \cdot x_2[L-1]\delta[m-L+1] \end{array}\right\} \tag{25}$$

Hence, equation (20) changes to $$x_1[n] + x_2[m] = \frac{1}{L}\{L \cdot x_1[n]\} + \frac{1}{L}\{L \cdot x_2[m]\} \tag{26}$$
$$= x_1[n] + x_2[m]$$

Figure 9:
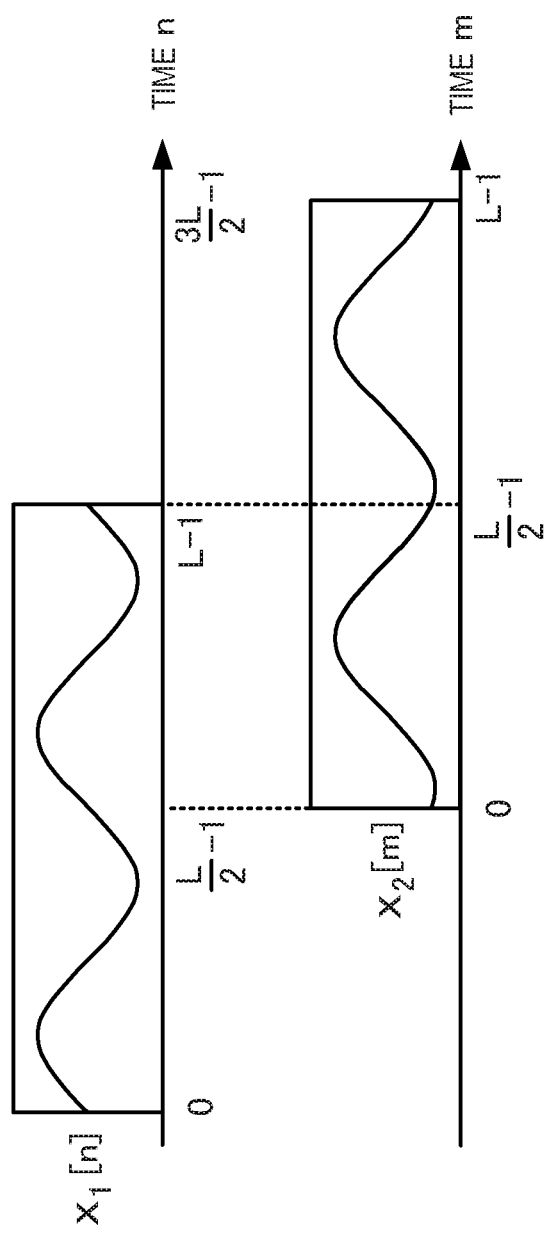
FIG. 9 is a view for explaining the operation of the phase controller according to the second embodiment of the present invention.
Figure 11:
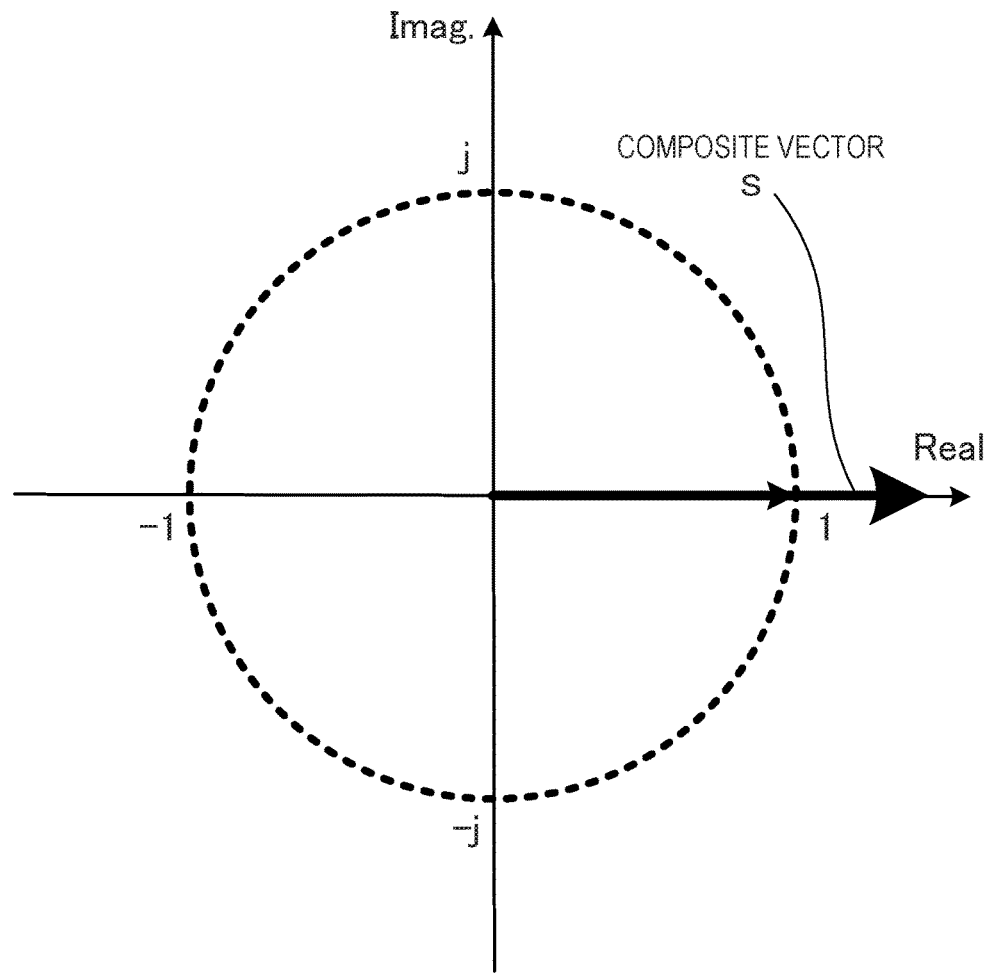
FIG. 11 is a view for explaining the operation of the phase controller according to the second embodiment of the present invention.

Consider a case where phase rotation is performed for the frequency domain signal X2[k]. At this time, a time domain signal as shown in FIG. 9 is obtained.

When the phase spectrum of X2[k] is rotated by φ[k], inverse transform is represented by $$x_2[m] = \frac{1}{L}\sum_{k=0}^{L-1} X_2[k]e^{j\phi[k]}e^{j2\pi\frac{m}{L}k} \tag{27}$$

When this is substituted into equation (18), $$x_1[n] + x_2[m] = \frac{1}{L}\sum_{k=0}^{L-1} X_1[k]e^{j2\pi\frac{n}{L}k} + \frac{1}{L}\sum_{k=0}^{L-1} X_2[k]e^{j\phi[k]}e^{j2\pi\frac{m}{L}k} \tag{28}$$
$$= \frac{1}{L}\sum_{k=0}^{L-1}\left(\sum_{n=0}^{L-1} x_1[n]e^{-j2\pi\frac{n}{L}k}\right)e^{j2\pi\frac{n}{L}k} +$$
$$\frac{1}{L}\sum_{k=0}^{L-1}\left(\sum_{m=0}^{L-1} x_2[m]e^{-(j2\pi\frac{m}{L}k+\phi[k])}\right)e^{j2\pi\frac{m}{L}k}$$

holds.

When this is expanded, $$x_1[n] + x_2[m] = \frac{1}{L}\left\{\begin{array}{c} x_1[0]\sum_{k=0}^{L-1} e^{j\frac{2\pi}{L}(n-0)k} + \\ x_1[1]\sum_{k=0}^{L-1} e^{j\frac{2\pi}{L}(n-1)k} + \ldots + \\ x_1[L-1]\sum_{k=0}^{L-1} e^{j\frac{2\pi}{L}(n-L+1)k} \end{array}\right\} + \tag{29}$$

$$\frac{1}{L}\left\{\begin{array}{c} x_2[0]\sum_{k=0}^{L-1} e^{j\frac{2\pi}{L}(m-0)k}e^{j\phi[k]} + \\ x_2[1]\sum_{k=0}^{L-1} e^{j\frac{2\pi}{L}(m-1)k}e^{j\phi[k]} + \ldots + \\ x_2[L-1]\sum_{k=0}^{L-1} e^{j\frac{2\pi}{L}(m-L+1)k}e^{j\phi[k]} \end{array}\right\}$$

holds.

Assume that the overlap ratio is 50%, and consider n=L/2 to L−1 of the overlap section. In the overlap section, equation (11) can be expanded to $$x_1\left[n+\frac{L}{2}\right] + x_2[m] = \frac{1}{L}\left\{\begin{array}{c} x_1\left[\frac{L}{2}\right]\sum_{k=0}^{L-1} e^{j\frac{2\pi}{L}(n+\frac{L}{2}-\frac{L}{2})k} + \\ x_1\left[\frac{L}{2}+1\right]\sum_{k=0}^{L-1} e^{j\frac{2\pi}{L}(n+\frac{L}{2}-1-\frac{L}{2}-1)k} + \ldots + \\ x_1[L-1]\sum_{k=0}^{L-1} e^{j\frac{2\pi}{L}(n-\frac{L}{2}-L+1-L+1)k} \end{array}\right\} + \tag{30}$$

$$\frac{1}{L}\left\{\begin{array}{c} x_2[0]\sum_{k=0}^{L-1} e^{j\frac{2\pi}{L}(n-0)k}e^{j\phi[k]} + \\ x_2[1]\sum_{k=0}^{L-1} e^{j\frac{2\pi}{L}(n-1)k}e^{j\phi[k]} + \ldots + \\ x_2\left[L-\frac{L}{2}-1\right]\sum_{k=0}^{L-1} e^{j\frac{2\pi}{L}(n-\frac{L}{2}-L+1)k}e^{j\phi[k]} \end{array}\right\}$$

$$= \frac{1}{L}\left\{\begin{array}{c} x_2[0]\sum_{k=0}^{L-1} e^{j\frac{2\pi}{L}nk} + \\ x_2[1]\sum_{k=0}^{L-1} e^{j\frac{2\pi}{L}nk} + \ldots + \\ x_2\left[L-\frac{L}{2}-1\right]\sum_{k=0}^{L-1} e^{j\frac{2\pi}{L}nk} \end{array}\right\} +$$

$$\frac{1}{L}\left\{\begin{array}{c} x_2[0]\sum_{k=0}^{L-1} e^{j\frac{2\pi}{L}(n-0)k}e^{j\phi[k]} + \\ x_2[1]\sum_{k=0}^{L-1} e^{j\frac{2\pi}{L}(n-1)k}e^{j\phi[k]} + \ldots + \\ x_2\left[L-\frac{L}{2}-1\right]\sum_{k=0}^{L-1} e^{j\frac{2\pi}{L}(n-\frac{L}{2}-L+1)k}e^{j\phi[k]} \end{array}\right\}$$

$$= \frac{1}{L}\left\{\begin{array}{c} x_2[0]\sum_{k=0}^{L-1} e^{j\frac{2\pi}{L}nk}(1+e^{j\phi[k]}) + \\ x_2[1]\sum_{k=0}^{L-1} e^{j\frac{2\pi}{L}(n-1)k}(1+e^{j\phi[k]}) + \ldots + \\ x_2\left[\frac{L}{2}-1\right]\sum_{k=0}^{L-1} e^{j\frac{2\pi}{L}(n-\frac{L}{2}-1)k}(1+e^{j\phi[k]}) \end{array}\right\}$$

Here, $$1 + e^{j\phi[k]} \tag{31}$$

parenthesized in each term represents vector composition, and can be drawn as in FIG. 10 when placing focus on the specific frequency k. If phase rotation is not performed, that is, when φ[k]=0, it can be drawn as in FIG. 11.

The absolute value of equation (31) is obtained as $$|1 + e^{j\phi[k]}| = |1 + \cos\phi[k] + j\sin\phi[k]| \qquad (32)$$
$$= \sqrt{(1+\cos\phi[k])^2 + \sin^2\phi[k]}$$
$$= \sqrt{1 + 2\cos\phi[k] + \cos^2\phi[k] + \sin^2\phi[k]}$$
$$= \sqrt{2(1+\cos\phi[k])}$$

Hence, the condition to maximize the absolute value of equation (31) is $\phi[k]=0$, and the value is 2. That is, when phase rotation is performed, the magnitude of the output signal becomes small, as is apparent. The correction amount calculator 503 decides the amplitude correction amount of the enhanced signal amplitude spectrum so as to correct the decrease amount of the output signal level.

A method of calculating a correction amount will be described here in detail assuming that the phase rotation amount is decided by a uniform random number. To simplify the problem, focus is placed on the variation in the magnitude caused by phase rotation, and each frequency component is assumed to have been normalized to a unit vector.

A case where phase rotation is not performed will be considered first. The composite vector in a case where the phase does not change between successive frames is represented by S shown in FIG. 11. The magnitude of the vector, |S| is given by $$|S| = \sqrt{\{1+1\}^2} \qquad (33)$$
$$= \sqrt{2^2}$$
$$= 2$$

On the other hand, when phase rotation is performed by a uniform random number, the phase differences $\phi$ between successive frames are uniformly distributed within the range of $-\pi$ to $+\pi$. The composite vector in a case where the phase changes between successive frames is represented by a vector S' shown in FIG. 10. The magnitude of the vector, |S'| is given by $$|S'| = \sqrt{\{1+\cos\phi\}^2 + \{\sin\phi\}^2} \qquad (34)$$
$$= \sqrt{2 + 2\{\cos\phi\}}$$

An expected value E(|S'|^2) is obtained as
$$E(|S'|^2) = E(2 + 2\cos\phi) = E(2) + E(2\cos\phi) \qquad (35)$$

Since the differences $\phi$ are uniformly distributed from $-\pi$ to $+\pi$, we obtain
$$E(2\cos(\phi))=0 \qquad (36)$$

For this reason, the expected value E(|S'|^2) is given by
$$E(|S'|^2)=2 \qquad (37)$$

Based on equation (33), the expected value E(|S'|^2) in a case where phase rotation is not performed is given by $$E(|S|^2) = E(2^2) \qquad (38)$$
$$= E(4)$$
$$= 4$$

When the ratio of equation (37) to equation (38) is calculated, $$E(|S'|^2)/E(|S|^2) = 2/4 \qquad (39)$$
$$= 1/2$$

holds.

That is, when the phase is rotated by a uniform random number, the power average value of the output signal decreases to ½ as compared to the input. The amplitude corrector 504 performs correction of the amplitude value. Hence, the correction amount calculator 503 obtains sqrt(2) as the correction coefficient and transmits it to the amplitude corrector 504.

Rotation amount generation by a uniform random number has been exampled above. The correction coefficient can also uniquely be determined using a normal random number if its variance and average value are determined. Correction coefficient derivation using a normal random number will be described below.

When a normal random number is used, the occurrence probability of $\phi$ is decided by a normal distribution. Hence, to obtain a power expected value in a case where phase rotation is executed using a normal random number, weighting needs to be performed based on the occurrence probability of $\phi$.

More specifically, a weight function $f(\phi)$ based on the occurrence probability of $\phi$ is introduced. By the weight function $f(\phi)$, $\cos(\phi)$ is weighted. The weighted value is further normalized by the integrated value of the weight function $f(\phi)$, thereby obtaining the power expected value.

By introducing the weight function $f(\phi)$ and its integrated value into equation (35) representing the output power expected value for a uniform random number, an output power expected value E(S''^2) in a case where phase rotation is performed using an normal random number can be expressed as $$E(|S''^2|) = E(2) + E\left(\frac{f(\phi)}{\int_{-\pi}^{\pi} f(\phi)\,d\phi}\cos(\phi)\right) \qquad (40)$$

Since the weight function $f(\phi)$ can be expressed as a normal distribution, $$f(\phi) = \frac{1}{\sqrt{2\pi}\,\sigma}\exp\left(-\frac{(\phi-\mu)^2}{2\sigma^2}\right) \qquad (41)$$

holds, where $\sigma$ is the variance, and $\mu$ is the average value.

For example, in a standard normal distribution in which the average value $\mu=0$, and the variance $\sigma=1$, $$f(\phi) = \frac{1}{\sqrt{2\pi}}\exp\left(-\frac{\phi^2}{2}\right) \qquad (42)$$

holds. When this is substituted into equation (40), we obtain $$E(|S^{\pi2}|) = E(2) + E\left(\frac{\exp\left(-\frac{\phi^2}{2}\right)}{\int_{-\pi}^{\pi}\exp\left(-\frac{\phi^2}{2}\right)d\phi}\cos(\phi)\right) \quad (43)$$

By numerical calculation of the second term of the right-hand side of equation (43), $$E(|S''|^2)=2\{1+0.609\}=3.218 \quad (44)$$

holds. Hence, the ratio to $E(|S^2|)$ in a case where phase rotation is not performed is given by $$E(|S''|^2)/E(|S|^2)=3.218/4=0.805 \quad (44)$$

In a case where the phase is rotated by a normal random number of a standard normal distribution, the correction amount calculator 503 obtains sqrt(1/0.805) as the correction coefficient and transmits it to the amplitude corrector 504. The phase rotation can be performed for all frequencies in the frame or for some frequencies where an abrupt change in the signal is detected. Amplitude correction is performed for a frequency that has undergone the phase rotation, that is, a frequency where an abrupt signal change is detected. Hence, the correction coefficient of a frequency that has not undergone the phase rotation is set to 1.0. Only the correction coefficient of the frequency that has undergone the phase rotation uses the value derived above.

As described above, in the amplitude controller 203, the amplitude correction coefficient is calculated using the phase rotation amount transmitted from the phase controller 202. The enhanced signal amplitude spectrum supplied from the noise suppressor 205 is multiplied by the correction coefficient and supplied to the inverter 204. This can eliminate lowering of the output level when the enhanced signal phase spectrum is obtained by rotating the noisy signal phase spectrum.

Note that the amplitude correction itself may be omitted if necessary, for example, if the calculated amplitude correction amount is negligible (the correction coefficient is close to 1.0), or the calculation amount in correction amount calculation and amplitude correction need to be decreased. At this time, only phase rotation by the phase rotator 501 is executed.

An example in which the phase is rotated using a random number has been described above. The same effect as described above can be obtained even by an arrangement that does not use a random number in a strict sense. The purpose of phase rotation is to eliminate or weaken a unique pattern that exists in the phase characteristic of an input noisy signal. Hence, any sequence capable of achieving the purpose can be used for phase rotation. For example, a sequence that has a period longer than the half of the frame length (the number of frequency components with independent amplitudes and power spectra) and a small correlation in one period can effectively be used.

<<Arrangement of Calculator and Abrupt Change Determiner>>

FIG. 12 is a block diagram for explaining the internal arrangement of the abrupt change determiner 209. As shown in FIG. 12, the abrupt change determiner 209 includes a parallelism calculator 1206 and a parallelism determiner 1207.

The parallelism calculator 1206 compares a gradient 1240 provided by the calculator 281 with an average value 1250 of weighted gradients provided by the calculator 283 on a frequency basis, and calculates the similarity of the gradients. That is, the parallelism of "the line calculated by the calculator 281" for the phase component signal in the frequency domain with respect to "the line calculated by the calculator 283" is calculated on a frequency basis. If the parallelism exceeds a predetermined value, the parallelism determiner 1207 determines that an abrupt signal change exists at the frequency.

If the determination is done not for each frequency but for each frequency band (sub-band) or frame, determination errors by phase components other than abrupt signal change components can be reduced by determination in boarder aspects. In addition, the determination result for each frequency may be corrected using the determination result for each frequency band or frame. For example, if the determination result for a certain frequency band indicates that "an abrupt signal change exists", the determination result for all frequencies within the frequency band is forcibly set to "an abrupt signal change exists", thereby reducing determination errors caused by disturbance of other signal components. To the contrary, if the determination result for a certain frequency band indicates that "no abrupt signal change exists", the determination result for all frequencies within the frequency band is forcibly set to "no abrupt signal change exists", thereby reducing determination errors caused by disturbance of other signal components. Alternatively, the ease (threshold) of determination for each frequency within the band may be corrected in a direction to easily determine "presence", and the configuration for independently performing determination for each frequency may be maintained in itself. When the determination result is obtained for each frequency or frequency band, an abrupt change can be suppressed for each frequency or frequency band. Hence, more accurate abrupt signal change suppression can be performed.

The abrupt change determiner 209 outputs abrupt signal change present (1) or abrupt signal change absent (0) as a determination result 1230. However, if the parallelism determiner 1207 outputs a value between 0 and 1 associated with the parallelism as the abrupt change presence score, the determination result 1230 is the value between 0 and 1, which represents the abrupt change presence score. In this case, likelihood (abrupt change presence) of inclusion of an abrupt signal change can be obtained. The presence score of an abrupt signal change can be obtained, for example, in the following way. First, each of the gradient 1240 provided by the calculator 281 and the average value 1250 of weighted gradients is converted into an angle corresponding to the gradient using an arctangent. The angle is assumed to range from −90° to 90°. The closer to 0 the absolute difference between the two angles is, the higher the presence score of an abrupt signal change is. The maximum value of the absolute difference between the two angles is 180°. Hence, a positive value is determined as a threshold. When the difference between the two angles exceeds the threshold, the score is 0. When the difference between the angles is 0, the score is 1. A general value of the possibility is defined as a function of the angle difference. The simplest function is a line. The presence score of an abrupt signal change is a value proportional to the difference between the two angles. The slope and y-intercept (function value when the difference between the two angles is 0) of the line are determined so as to meet a boundary condition when the angle difference equals 0 or 1. As the function, an arbitrary linear or nonlinear function or polynomial may be used.

Figure 13:
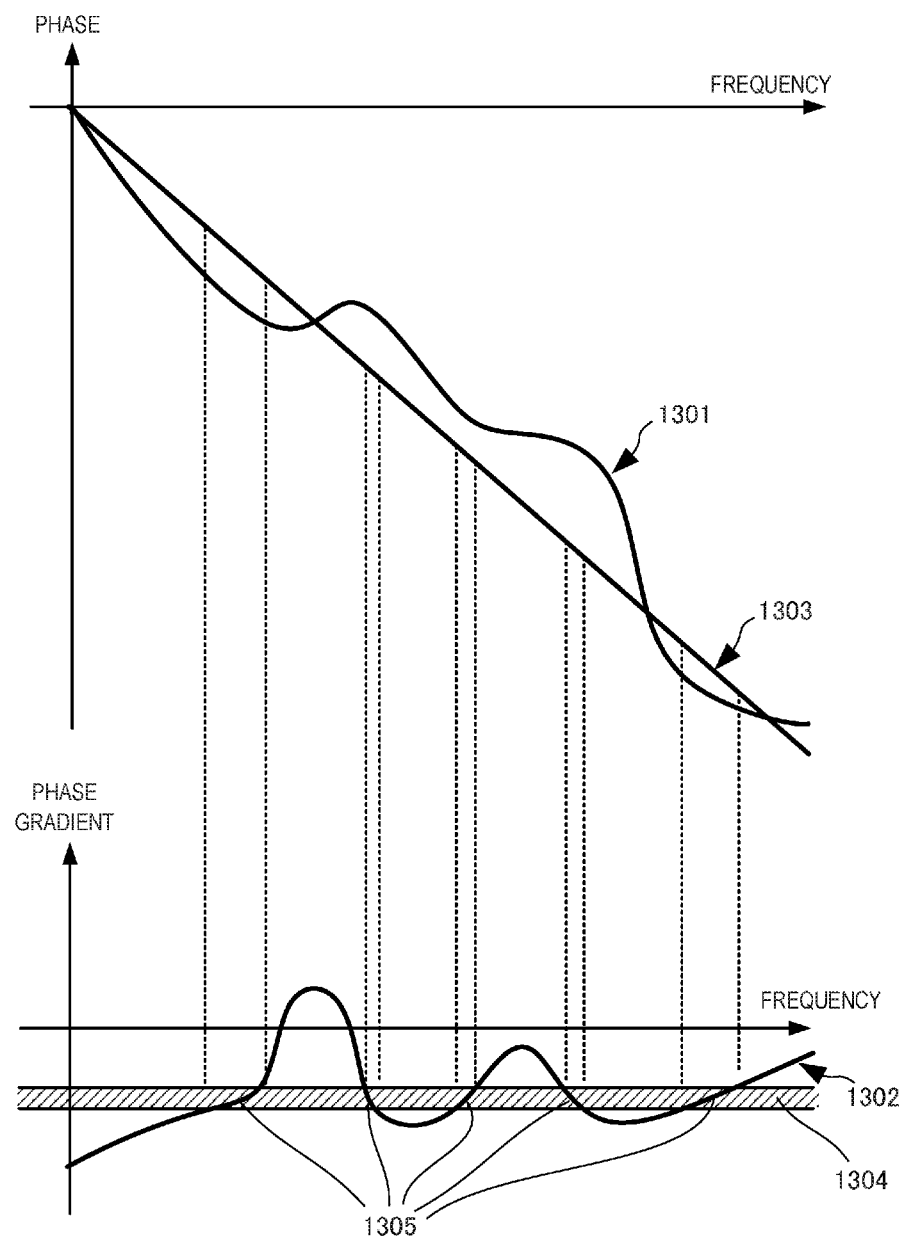
FIG. 13 is a graph for explaining processing of the calculator according to the second embodiment of the present invention.

FIG. 13 is a graph showing a phase and its change amount. When the phase changes along the frequency axis in the frequency domain, like a graph 1301, the phase change amount changes as indicated by a graph 1302 along the frequency axis in the frequency domain.

On the other hand, a phase represented by a line 1303 in the frequency domain can be calculated as a regression line on the graph 1301. This is equivalent to averaging the gradients at points on the graph 1301 and setting a line having the obtained average value as the slope to the line 1303.

In this embodiment, the presence of an abrupt signal change is determined based on how parallel the phase component signal 1301 and the line 1303 are.

When the phase gradient is plotted along the ordinate, and the frequency is plotted along the abscissa, a range approximate to the slope of the line 1303 is represented by a range 1304. Hence, if an overlapping portion 1305 between the range 1304 and the graph 1302 is larger than a predetermined threshold, the abrupt change determiner 209 determines that an abrupt change in the signal exists.

Figure 14:
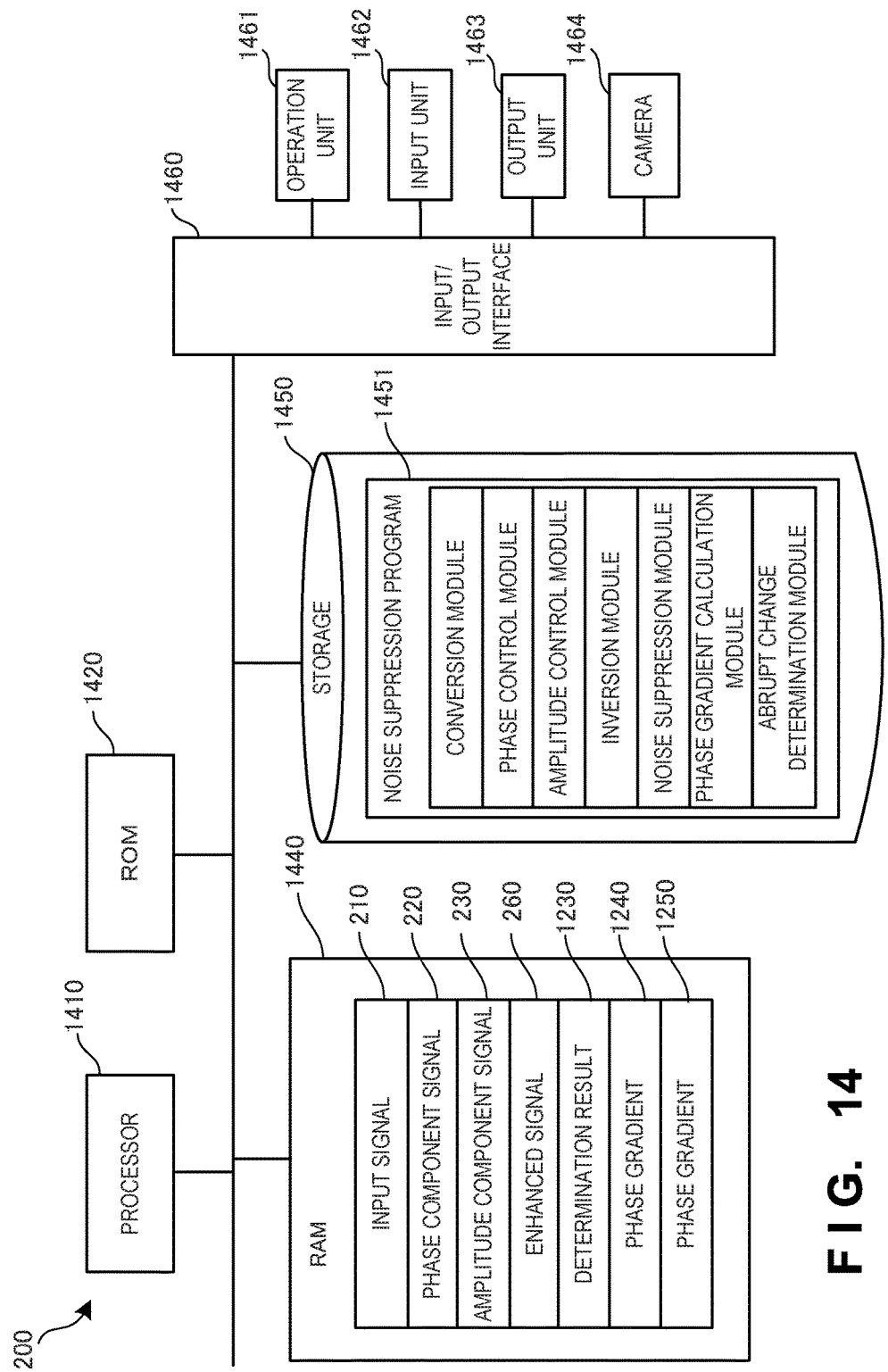
FIG. 14 is a block diagram showing the hardware arrangement of the noise suppression apparatus according to the second embodiment of the present invention.

FIG. 14 is a block diagram for explaining a hardware arrangement when the noise suppression apparatus 200 according to this embodiment is implemented using software.

The noise suppression apparatus 200 includes a processor 1410, a ROM (Read Only Memory) 1420, a RAM (Random Access Memory) 1440, a storage 1450, an input/output interface 1460, an operation unit 1461, an input unit 1462, and an output unit 1463. The noise suppression apparatus 200 may include a camera 1464. The processor 1410 is a central processing unit and executes various programs, thereby controlling the overall noise suppression apparatus 200.

The ROM 1420 stores various parameters as well as a boot program to be executed first by the processor 1410. The RAM 1440 includes an area to store an input signal 210, the phase component signal 220, the amplitude component signal 230, and the enhanced signal 260 as well as a program load area (not shown). The RAM 1440 also includes an area to store the determination result 1230, the phase gradients 1240 and 1250, and the like.

The storage 1450 stores a noise suppression program 1451. The noise suppression program 1451 includes a conversion module, a phase control module, an amplitude control module, an inversion module, a noise suppression module, a phase gradient calculation module, and an abrupt change determination module. When the processor 1410 executes the modules included in the noise suppression program 1451, the functions of the converter 201, the phase controller 202, the amplitude controller 203, the inverter 204, the noise suppressor 205, the calculators 281 and 283, the weighting unit 285, and the abrupt change determiner 209 shown in FIG. 2 can be implemented. Note that the storage 1450 may store a noise database.

An enhanced signal that is the output of the noise suppression program 1451 executed by the processor 1410 is output from the output unit 1463 via the input/output interface 1460. This can suppress, for example, the operation sound of the operation unit 1461 input from the input unit 1462. Also possible is an application method of, for example, detecting abrupt signal change inclusion in the input signal input from the input unit 1462 and starting shooting by the camera 1464.

FIG. 15A is a flowchart for explaining the procedure of abrupt signal change determination processing of the noise suppression program 1451. In step S1501, the calculator 281 executes phase gradient calculation processing in the frequency domain. In step S1503, the weighting unit 285 executes weighting processing of weighting the phase gradient in the frequency domain by the amplitude. In step S1505, the calculator 283 executes weighted phase gradient average value calculation processing in the frequency domain.

In step S1507, the calculated gradients are compared on a frequency basis. In step S1509, it is determined whether the absolute difference between the gradients is equal to or smaller than a predetermined threshold N. If the absolute difference is N or less, the process advances to step S1511 to set a flag (set I(k)=1) for a frequency k. On the other hand, if the absolute difference is not N or less, I(k)=0 is set in step S1514. In step S1515, it is determined whether k=F (F is the number of frequency components in the entire frame). If k≠F, the process advances to step S1517 to set k=k+1. The process then returns to step S1507 to compare the gradients on a frequency basis throughout the frame. Finally in step S1519, it is determined that an abrupt signal change exists at the frequency k when I(k)=1, and the determination result is supplied to the noise suppressor 205 and the phase controller 202. Note that in place of step S1519, I(k) may be integrated in the frame, and when the integral value of I(k) exceeds a predetermined threshold, the abrupt change determiner 209 may determine that the frame includes an abrupt signal change. At this time, the abrupt change determination result may be hanged over and integrated in the next frequency band.

As a hangover function, the threshold N in the next frame may be set small. When the threshold in the next frame is thus set, it is possible to easily detect an abrupt signal change (impulsive sound) and reduce detection omissions.

Figure 15B:
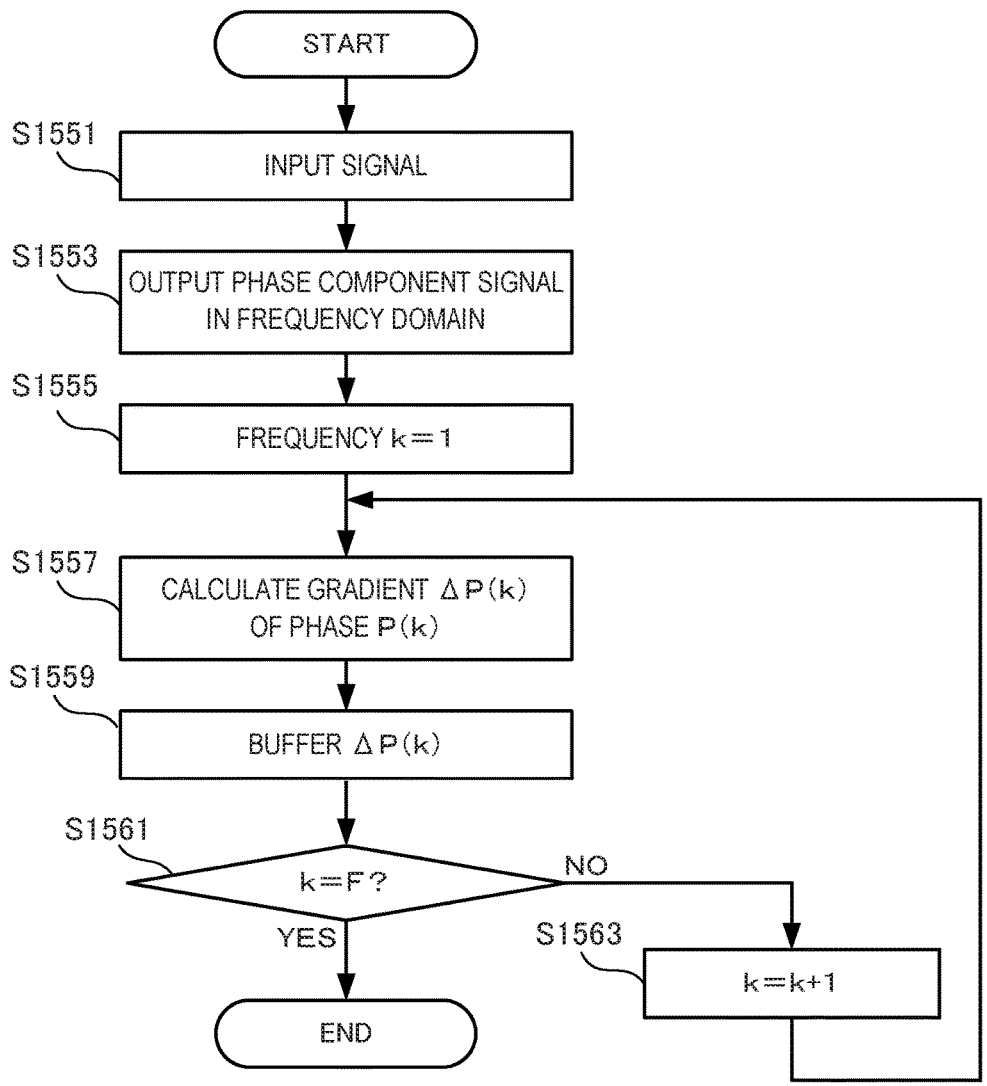
FIG. 15B is a flowchart for explaining the procedure of processing of the noise suppression apparatus according to the second embodiment of the present invention.

FIG. 15B is a flowchart for explaining the procedure of gradient calculation processing performed by the calculator 281. When a signal is input in step S1551, the process advances to step S1553. After frame division and windowing, Fourier transform is performed to extract the phase component signal in the frequency domain. In step S1555, the step k of the frequency is set to 1. In step S1557, a phase P(k) is differentiated to calculate a gradient ΔP(k). In step S1559, the gradient is buffered. In step S1561, it is determined whether k=F (F is the number of frequency components in the entire frame). If k≠F, the process advances to step S1563 to set k=k+1. The process then returns to step S1557 to calculate the gradient on a frequency basis throughout the frame.

Figure 15C:
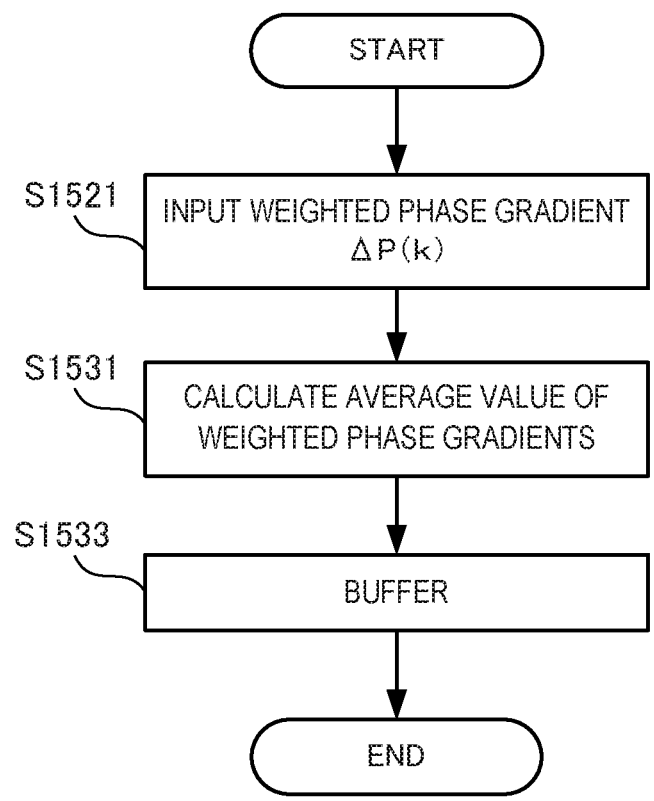
FIG. 15C is a flowchart for explaining the procedure of processing of the noise suppression apparatus according to the second embodiment of the present invention.

FIG. 15C is a flowchart for explaining the procedure of weighted gradient average value calculation processing performed by the calculator 283. When a weighted phase gradient is input in step S1521, the average value of weighted phase gradients is calculated in step S1531. In step S1533, the phase gradient and the average value of weighted phase gradients are buffered.

With the above-described processing, an abrupt signal change can more correctly be detected, and the abrupt change portion can appropriately be suppressed as needed. Note that in this embodiment, the phase gradient is obtained as a differential value. However, another index such as the rotation amount of a unit vector may be obtained and used for determination.

Third Embodiment

Figure 16:
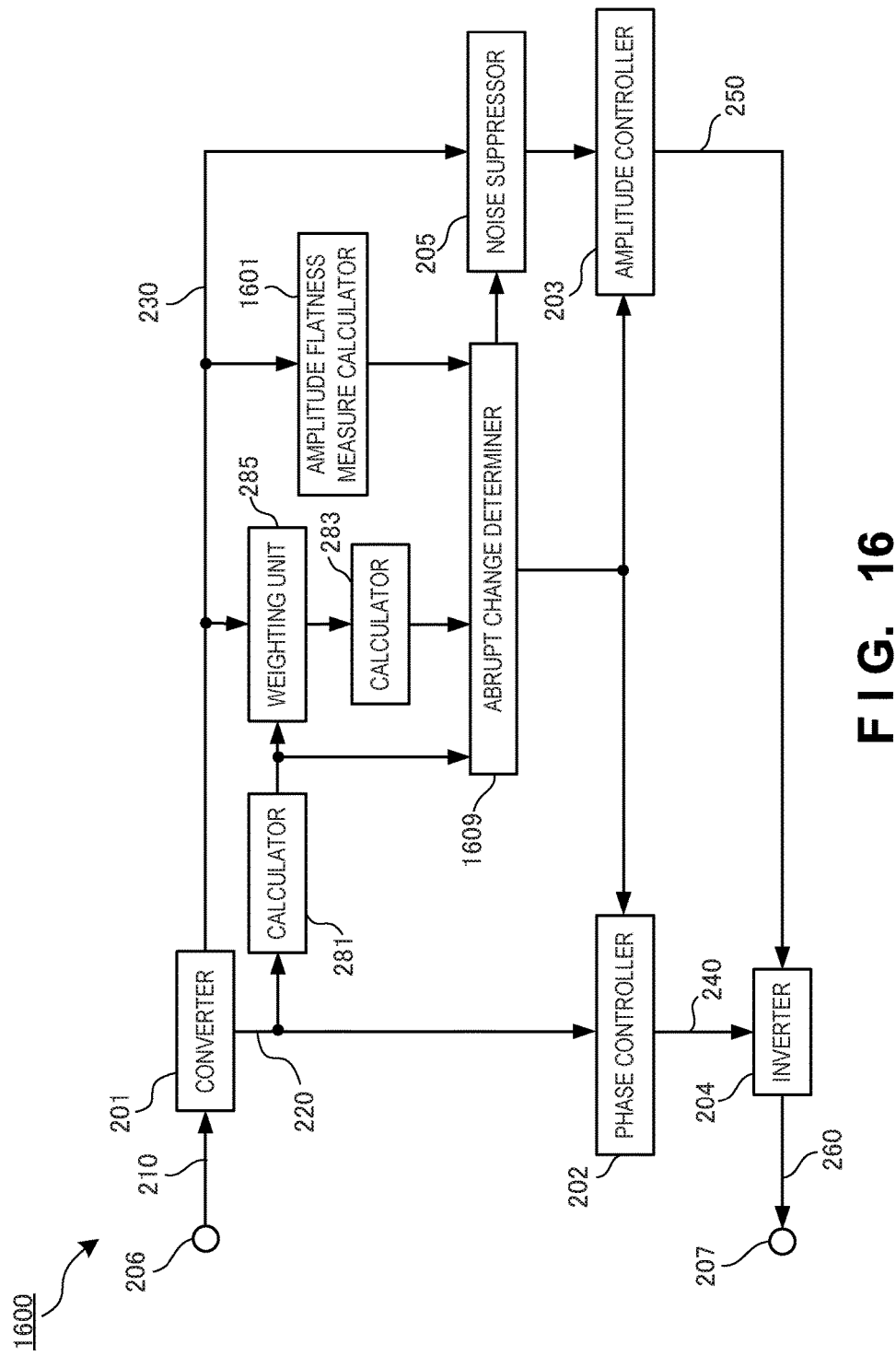
FIG. 16 is a block diagram showing the arrangement of a noise suppression apparatus according to the third embodiment of the present invention.

A noise suppression apparatus 1600 according to the third embodiment of the present invention will be described next with reference to FIG. 16. FIG. 16 is a block diagram for explaining the functional arrangement of the noise suppression apparatus 1600 according to this embodiment. The noise suppression apparatus 1600 according to this embodiment is different from the second embodiment in that an amplitude flatness measure calculator 1601 is additionally provided. The rest of the components and operations is the same as in the second embodiment. Hence, the same reference numerals denote the same components and operations, and a detailed description thereof will be omitted.

The amplitude flatness measure calculator 1601 calculates an amplitude change along the frequency axis and supplies it to an abrupt change determiner 1609. A frequency whose amplitude change with respect to an adjacent frequency is small represents an abrupt signal change. As the amplitude change, one flatness measure may be obtained for each band or all frequencies. More specifically, FM (Flatness Measure) representing a flatness measure is obtained by $$FM = \frac{\sqrt[N]{\prod_{n=0}^{N-1} x(n)}}{\frac{\sum_{n=0}^{N-1} x(n)}{N}} = \frac{\exp\left(\frac{1}{N}\sum_{n=0}^{N-1} \ln x(n)\right)}{\frac{1}{N}\sum_{n=0}^{N-1} x(n)} \quad (46)$$

where x(n) is the amplitude or power spectrum at a frequency n, and N is the number of frequency components included in the flatness measure calculation section.

FM takes a value of 0.0 to 1.0. If the amplitude is completely flat, FM is 1.0. The flatness measure is disclosed in non-patent literature 3.

The flatness measure can also be expressed using another index. For example, it is possible to obtain the average of x(n) for each band or all frequencies and calculate the sum of squared differences of x(n) of each frequency component n and the average value as the flatness measure for each band or all frequencies.

One sum of squared differences may be obtained not for all frequencies but in a single or a plurality of frequency bands and used as the flatness measure. The thus obtained flatness measure has a value of 0.0 if the amplitude is completely flat, and takes a larger value as the flatness measure lowers.

A smoothness may be used as another index of the flatness measure. The smoothness can be expressed as the sum of absolute differences between adjacent samples along the frequency axis. The smoothness takes a large value for a waveform having large unevenness (not smooth), and a small value for a waveform having small unevenness (smooth). This index is known as TV (Total Variation).

As the flatness measure, a flatness measure along the frequency axis is used above. However, a flatness measure along the time axis is also usable. In an abrupt signal change portion, the amplitude and power abruptly increase. Using this characteristic, an abrupt signal change can be determined to exist when the flatness measure along the time axis is low. More specifically, if the amplitude or power difference between the current frame and the immediately preceding frame is a predetermined value or more, it is determined that the flatness measure is low, that is, an abrupt signal change exists. Alternatively, the amplitude or power difference between adjacent frames may be obtained for a plurality of frames including several past frames and the current frame, and the result of linearly or nonlinearly combining the differences may be defined as the flatness measure. When the information of the past frames is used, a blunted abrupt signal change portion including low frequency components can easily be detected, and the suppression performance can be improved. Note that when calculating the amplitude or power difference between adjacent frames, the calculation may be done for each frequency component, band, or all frequencies. The amplitude or power difference can also be calculated for a single or a plurality of bands. For example, when the amplitude or power difference can also be calculated in a single band, particularly, in a high frequency band, the influence of speech and other signals can be reduced, and the abrupt signal change portion can more correctly be detected.

The above-described two flatness measures, that is, the flatness measure along the frequency axis and the flatness measure along the time axis can be used singly or in combination. As examples of combination, an abrupt signal change portion is detected based on linear or nonlinear combination of the two flatness measures, or detection results based on the flatness measures are combined. It is determined that an abrupt signal change is detected when the flatness measure in the frequency direction is large or the flatness measure in the time direction is small. Hence, when combining, a contrivance such as changing one of the flatness measures to a reciprocal is needed.

The substantial function of the amplitude flatness measure calculator 1601 is to obtain the possibility of the presence of an abrupt signal change using amplitude information, and may therefore be replaced with another method. Techniques of detecting an abrupt signal change using amplitude information are disclosed in non-patent literatures 6, 7, and 8.

The abrupt change determiner 1609 determines an abrupt change in the signal in consideration of two indices, that is, the similarity of gradients (parallelism) and the amplitude flatness measure. This is because when the amplitude is flat (variation is small) along the frequency axis, an abrupt signal change portion is assumed to exist at a high possibility. This is self-evident from the fact that the abrupt signal change is impulsive (the amplitude increases and decreases in a short time), and the Fourier transform of the impulse yields a white signal (the amplitude and power are equal throughout the frequencies). As the determination method, for example, one of the following methods can be selected.

(1) If both the parallelism and the amplitude flatness measure meet corresponding conditions (for example, the gradient difference value is N=0.1 or less, and the amplitude flatness measure FM is M=0.8 or more), it is determined that an abrupt change in the signal exists.

(2) The OR of determination results obtained by solely using the parallelism and the amplitude flatness measure is used. To calculate possibility of the presence of an abrupt signal change, determination is performed based on a larger one (or smaller one) of the possibility determined by using the parallelism and the possibility determined by using the amplitude flatness measure.

(3) If the averages of both the parallelisms and the amplitude flatness measures meet a condition (for example, an average AV1 of a gradient difference value PX and a difference value QX between 1.0 and the amplitude flatness measure FM, that is, QX=(1.0−FM) is AV1=(PX+QX)/2=0.1 or less), it is determined that an abrupt change in the signal exists.

(4) If a value obtained by combining the gradient difference value and the amplitude flatness measure while adding weights to them meets a compound condition (for example, a weighted average AV2 of the gradient difference value PX and the difference value QX between 1.0 and the amplitude flatness measure FM, that is, QX=(1.0−FM) is AV2=(0.8× PX+0.2×QX)=0.1 or less), it is determined that an abrupt change in the signal exists.

(5) If the gradient difference value and the amplitude flatness measure are combined using a linear or nonlinear function, and the result of combination is larger than a predetermined value, it is determined that an abrupt change in the signal exists. If an amplitude flatness measure in the time direction is included, its reciprocal is used in place of the amplitude flatness measure.

(6) Only one of the gradient difference value and the amplitude flatness measure, which is close to an ideal value (the difference value is ideally smaller, and the flatness measure is ideally larger) is used, and if the value closer to the ideal value meets a condition, it is determined that an abrupt change in the signal exists. If an amplitude flatness measure in the time direction is included, its reciprocal is used in place of the amplitude flatness measure.

(7) If information about the amplitude or power spectrum of an abrupt change signal to be detected is obtained in advance, and the amplitude or power spectrum is flat, the weight of the gradient difference value is made small.

(8) If information about the amplitude or power spectrum of an abrupt change signal to be detected is obtained in advance, and the amplitude or power spectrum of the input noisy signal is smaller than the minimum value of the amplitude or power spectrum, the threshold used to detect an abrupt signal change is temporarily largely changed to make detection hard.

When processing a specific signal, for example, when detecting/suppressing an impulsive sound of small noise close to an impulse, information about the amplitude or power is sometimes more reliable than phase information. For example, when detecting a gunshot of a pistol in a quiet environment, the detection may be performed using only the amplitude. On the other hand, when the amplitude or power spectrum of noise largely changes, for example, when detecting a gunshot in airport security, it is effective to change the weights of the amplitude and phase between a quiet situation (with small noise) and a situation with large noise. In this case, the weights of the amplitude and phase may be changed in accordance with the presence/absence of noise or time zone. For example, if the latest information of flight schedule can be acquired from the control tower, the takeoff and landing times of airplanes are known. Hence, at a timing of airplane arrival (timing with much noise), the phase to which a large weight is added can be used to detect a gunshot. This is because in a case where signals other than a gunshot (impulsive sound to be detected) coexist, impulsive sound detection using phase information is more effective than detection using an amplitude.

On the other hand, in a situation with small noise, the impulsive sound can effectively be detected by performing determination while attaching importance to the absolute value of the frequency domain vector, that is, the amplitude value of an input noisy signal. In this case as well, the power spectrum value may be used in place of the amplitude spectrum, as a matter of course. The amplitude of the impulsive sound is not flat in some cases depending on the type of the signal. In this case, when detection is performed while making the weight of the phase flatness measure large, an abrupt change in the signal can accurately be detected. If information about the amplitude or power spectrum of an impulsive sound is obtained in advance, the amplitude flatness measure calculation result can be corrected using the obtained information so as to obtain the same result as in a case where the amplitude is flat. More specifically, the amplitude flatness measure is calculated after the amplitude spectrum 230 is multiplied for each frequency component by the reciprocal of the amplitude or power spectrum shape of an impulsive sound.

As described above, according to this embodiment, an abrupt signal change portion can be detected using the amplitude flatness measure together. With this processing, an abrupt signal change (impulsive sound) can more correctly be detected, and the abrupt signal change (impulsive sound) can appropriately be suppressed as needed.

Fourth Embodiment

Note that in the above embodiments, a case where an abrupt signal change detection method is applied to a noise suppression apparatus aiming at suppressing an abrupt signal change portion has been described. However, the present invention is not limited to this. The abrupt signal change detection method is usable in various apparatuses, systems, and situations aiming at detecting an impulsive sound (a signal that abruptly rises and immediately falls). In addition, a signal that abruptly rises (or falls) and remains intact can also be detected as an abrupt change portion.

For example, a present audio encoding method (for example, encoder of MPEG AAC) employs an information compression method different from normal for an abrupt signal change portion called an attack. The method is also applicable to detect the abrupt signal change portion. In the abrupt signal change portion, the analysis window length is changed, and preceding noise called a pre-echo is suppressed. Hence, the abrupt signal change portion needs to be detected. As compared to a method of doing detection using a change in the amplitude or entropy, it is possible to accurately detect an abrupt change and effectively compress information.

Figure 17:
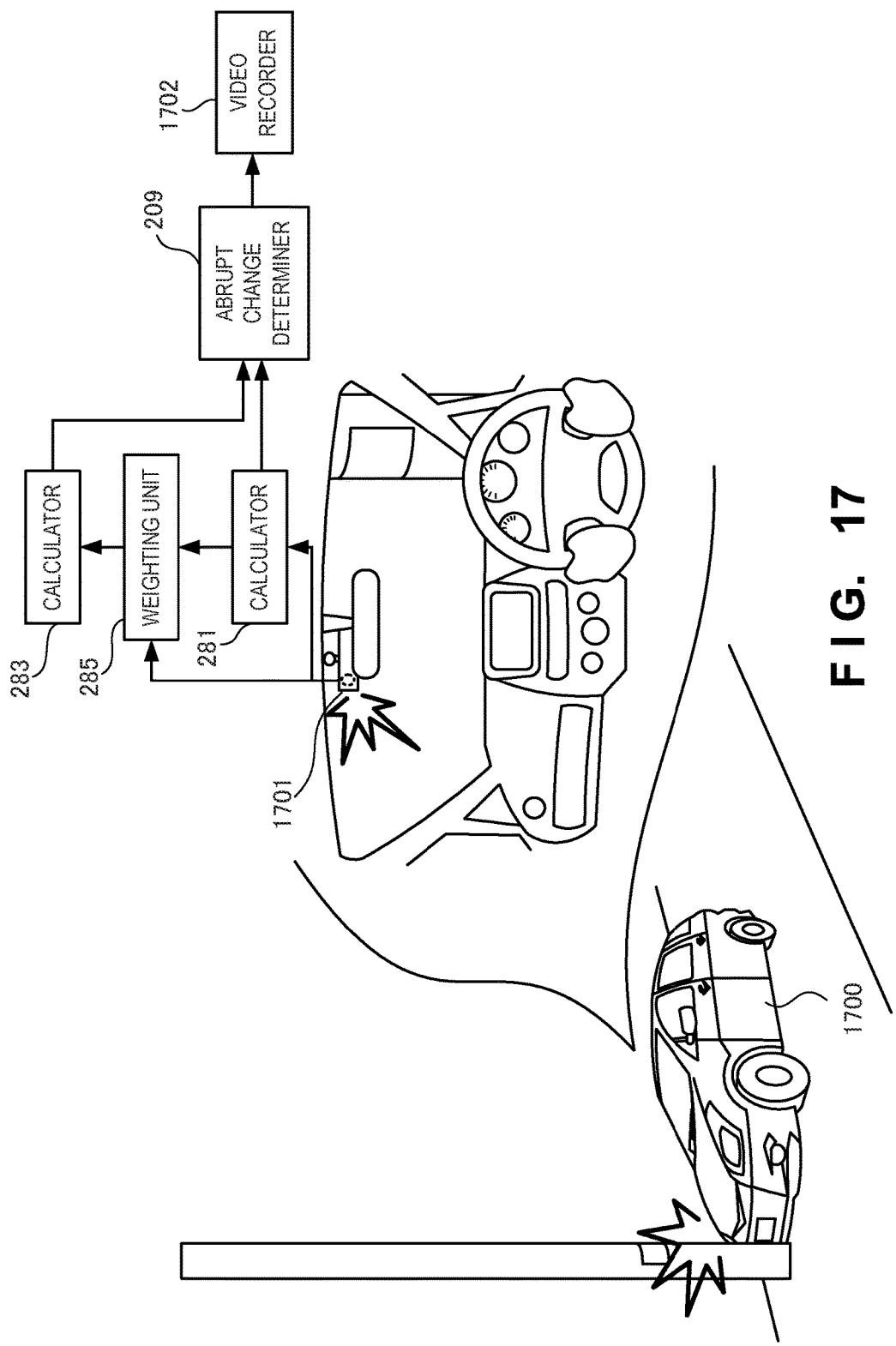
FIG. 17 is a view for explaining an application example according to the fourth embodiment of the present invention.

It is also possible to assume an application example in which a microphone 1701, calculators 281 and 283, a weighting unit 285, an abrupt change determiner 209, and a video recorder 1702 are provided aboard a vehicle 1700, as shown in FIG. 17. Triggered by impulsive sound detection, the video recorder 1702 prohibits an image shot by a camera from being overwritten and saved, thereby leaving the record of an accident situation. At this time, overwrite saving may be prohibited after a delay of a predetermined time from impulsive sound detection. Unlike a case where an impulsive sound itself is used as a trigger, an accident situation can automatically be recorded even when the impact is small, or another vehicle is involved in an accident.

Also assume an application example in which the calculators 281 and 283, the weighting unit 285, the abrupt change determiner 209, and an alarm unit 1801 are connected to an electrocardiograph 1800, as shown in FIG. 18. It is possible to more correctly and effectively detect an abnormal heartbeat in an electrocardiogram. In particular, this configuration is effective in a case where much noise is included. This method is also applicable to monitor the echo of an embryo. In some cases, a heart sound cannot correctly be monitored due to disturbance of noise. This technique is effective in such a case. That is, the technique is widely applicable to detect an abrupt change in a biomedical signal.

Figure 20:
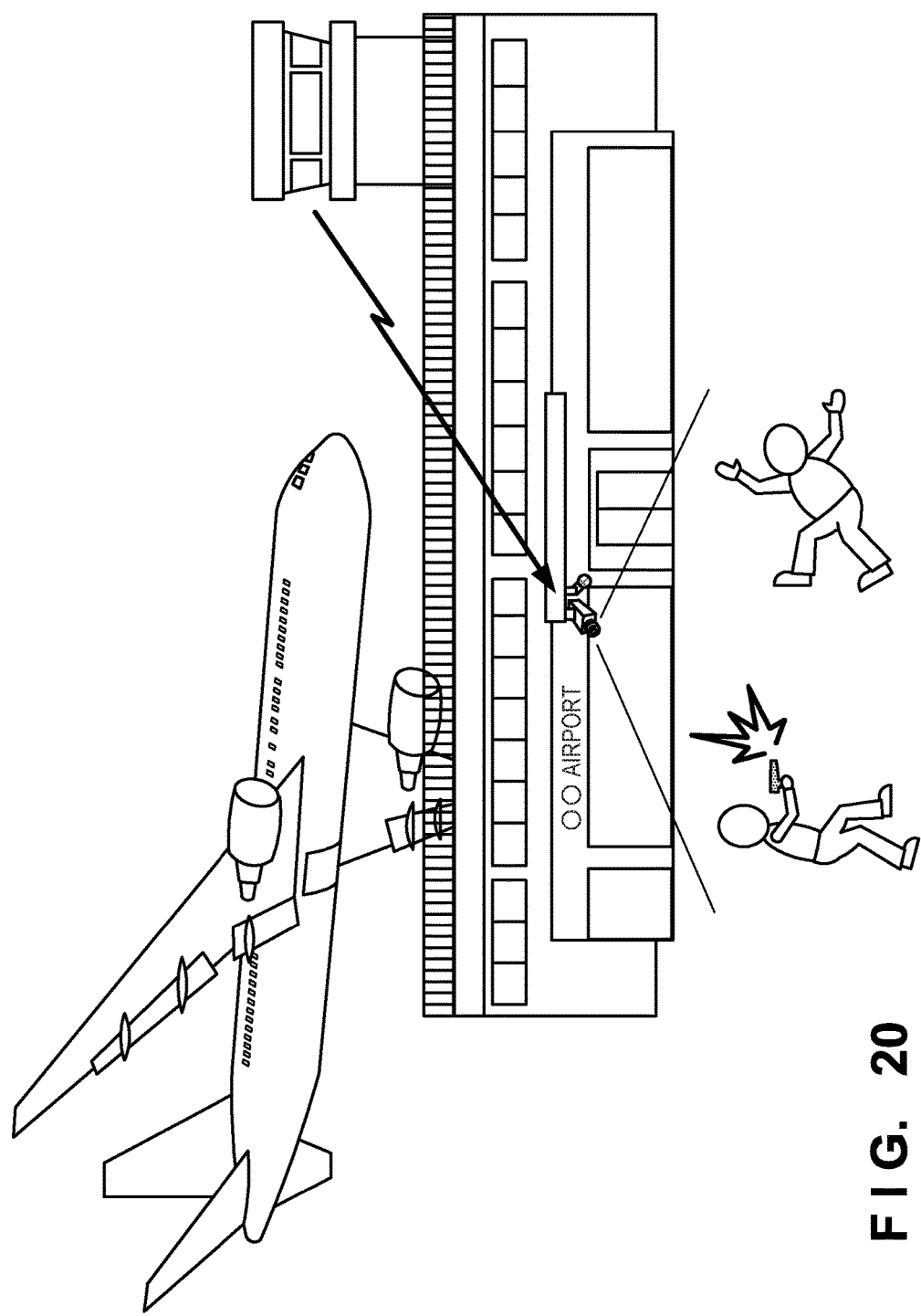
FIG. 20 is a view for explaining an application example according to the fourth embodiment of the present invention.

Similarly, impulsive sound detection according to the present invention may be used to detect an abnormality in a hard disk drive 1900, as shown in FIG. 19. The present invention may also be used to detect a gunshot or explosion sound in a situation with loud noise, for example, in an airport, as shown in FIG. 20.

Other Embodiments

While the present invention has been described with reference to exemplary embodiments, it is to be understood that the invention is not limited to the disclosed exemplary embodiments. The arrangement and details of the present invention can variously be modified without departing from the spirit and scope thereof, as will be understood by those skilled in the art. The present invention also incorporates a system or apparatus that combines different features included in the embodiments in any form.

The present invention is applicable to a system including a plurality of devices or a single apparatus. The present invention is also applicable even when a signal processing program for implementing the functions of the embodiments is supplied to the system or apparatus directly or from a remote site. Hence, the present invention also incorporates the program installed in a computer to implement the functions of the present invention by the computer, a medium storing the program, and a WWW (World Wide Web) server that causes a user to download the program. In particular, the present invention incorporates a non-transitory computer readable medium.

Other Expressions of Embodiments

Some or all of the above-described embodiments can also be described as in the following supplementary notes but are not limited to the followings.

(Supplementary Note 1)

There is provided a signal processing apparatus comprising:

a converter that converts an input signal into a phase component signal in a frequency domain;

a first calculator that calculates a phase gradient of the phase component signal for each of a plurality of frequencies as a first phase gradient;

a weighting unit that weights the first phase gradient with an amplitude or a power of the input signal, thereby calculating a weighted first phase gradient;

a second calculator that calculates a second phase gradient based on the weighted first phase gradient; and a determiner that determines presence of an abrupt change in the input signal based on the first phase gradient and the second phase gradient.

(Supplementary Note 2)

There is provided the signal processing apparatus according to claim 1, wherein said determiner determines the presence of an abrupt change in the input signal based on a similarity between the first phase gradient and the second phase gradient.

(Supplementary Note 3)

There is provided the signal processing apparatus according to claim 1 or 2, wherein said second calculator obtains, as the second phase gradient, an average value of the weighted first phase gradients at the plurality of frequencies.

(Supplementary Note 4)

There is provided the signal processing apparatus according to claim 1 or 2, wherein said second calculator obtains, as the second phase gradient, an average value of the weighted first phase gradients at frequencies in which speech is not dominant.

(Supplementary Note 5)

There is provided the signal processing apparatus according to claim 1 or 2, wherein said second calculator obtains, as the second phase gradient, an average value of the weighted first phase gradients at frequencies in which speech is not dominant, and one of the amplitude and the power is larger than background noise.

(Supplementary Note 6)

There is provided the signal processing apparatus according to any one of claims 1 to 5, wherein said converter further calculates an amplitude component signal of the input signal in the frequency domain, and the signal processing apparatus further comprises a calculator that calculates a flatness measure of the amplitude component signal, and said determiner further determines the presence of an abrupt change in the input signal in consideration of the flatness measure of the amplitude component signal.

(Supplementary Note 7)

There is provided the signal processing apparatus according to claim 6, wherein said determiner determines the presence of an abrupt change in the input signal based on values obtained by weighting the similarity between the first phase gradient and the second phase gradient and the flatness measure of the amplitude component signal.

(Supplementary Note 8)

There is provided the signal processing apparatus according to any one of claims 1 to 7, further comprising an amplitude controller that suppresses the amplitude to a degree corresponding to the presence of an abrupt change.

(Supplementary Note 9)

There is provided a signal processing method comprising:

converting an input signal into a phase component signal in a frequency domain;

calculating a first phase gradient for each of a plurality of frequencies of the phase component signal;

weighting the first phase gradient with an amplitude or a power of the input signal, thereby calculating a weighted first phase gradient;

calculating a second phase gradient using the weighted first phase gradients; and determining presence of an abrupt change in the input signal based on the first phase gradients and the second phase gradient.

(Supplementary Note 10)

There is provided a signal processing program for causing a computer to execute a method comprising:

converting an input signal into a phase component signal in a frequency domain;

calculating a first phase gradient for each of a plurality of frequencies of the phase component signal;

weighting the first phase gradient by one of an amplitude and a power of the frequency, thereby calculating a weighted first phase gradient;

calculating a second phase gradient using the weighted first phase gradients; and determining presence of an abrupt change in the input signal based on the first phase gradients and the second phase gradient.

This application claims the benefit of Japanese Patent Application No. 2013-180735, filed on Aug. 30, 2013, which is hereby incorporated by reference in its entirety.

The invention claimed is:

1. A signal processing apparatus comprising:

a converter that converts an input signal into a phase component signal in a frequency domain;

a first calculator that calculates a first phase gradient of the phase component signal for each of a plurality of frequencies;

a weighting unit that weights the first phase gradient with an amplitude or a power of the input signal to obtain a weighted first phase gradient;

a second calculator that calculates a second phase gradient at a plurality of frequencies as an average of the weighted first phase gradients; and a determiner that determines, at a plurality of frequencies, presence of an abrupt change in the input signal based on the first phase gradient and the second phase gradient.

2. The signal processing apparatus according to claim 1, wherein said determiner determines the presence of an abrupt change in the input signal based on a similarity between the first phase gradient and the second phase gradient.

3. The signal processing apparatus according to claim 1, wherein said second calculator obtains, as the second phase gradient, an average value of the weighted first phase gradients at the plurality of frequencies.

4. The signal processing apparatus according to claim 1, wherein said second calculator obtains, as the second phase gradient, an average value of the weighted first phase gradients at frequencies in which speech is not dominant.

5. The signal processing apparatus according to claim 1, wherein said second calculator obtains, as the second phase gradient, an average value of the weighted first phase gradients at frequencies in which speech is not dominant, and one of the amplitude and the power is larger than background noise.

6. The signal processing apparatus according to claim 1, wherein
said converter further calculates an amplitude component signal of the input signal in the frequency domain, and the signal processing apparatus further comprises a calculator that calculates a flatness measure of the amplitude component signal, and said determiner further determines the presence of an abrupt change in the input signal in consideration of the flatness measure of the amplitude component signal.

7. The signal processing apparatus according to claim 6, wherein said determiner determines the presence of an abrupt change in the input signal based on values obtained by weighting a similarity between the first phase gradient and the second phase gradient and the flatness measure of the amplitude component signal.

8. The signal processing apparatus according to claim 1, further comprising an amplitude controller that suppresses the amplitude to a degree corresponding to the presence of an abrupt change.

9. A signal processing method comprising:
converting an input signal into a phase component signal in a frequency domain;
calculating a first phase gradient for each of a plurality of frequencies of the phase component signal;
weighting the first phase gradient with an amplitude or a power of the input signal to obtain a weighted first phase gradient;
calculating a second phase gradient at a plurality of frequencies as an average of the weighted first phase gradients; and
determining, at a plurality of frequencies, presence of an abrupt change in the input signal based on the first phase gradients and the second phase gradient.

10. The signal processing method according to claim 9, wherein determining the presence of an abrupt change in the input signal includes determining a similarity between the first phase gradient and the second phase gradient.

11. The signal processing method according to claim 9, wherein calculating the second phase gradient includes determining an average value of the weighted first phase gradients at the plurality of frequencies.

12. The signal processing method according to claim 9, wherein calculating the second phase gradient includes determining an average value of the weighted first phase gradients at frequencies in which speech is not dominant.

13. The signal processing method according to claim 9, wherein calculating the second phase gradient includes determining an average value of the weighted first phase gradients at frequencies in which speech is not dominant, and one of the amplitude and the power is larger than background noise.

14. The signal processing method according to claim 9, further including:
calculating an amplitude component signal of the input signal in the frequency domain;
calculating a flatness measure of the amplitude component signal; and
determining the presence of an abrupt change in the input signal based on the flatness measure.

15. The signal processing method according to claim 14, further including:
determining the presence of an abrupt change in the input signal based on values obtained by weighting a similarity between the first phase gradient and the second phase gradient and the flatness measure of the amplitude component signal.

16. The signal processing method according to claim 9, further including suppressing the amplitude to a degree corresponding to the presence of an abrupt change.

17. A non-transitory computer readable medium storing a signal processing program for causing a computer to execute a method comprising:
converting an input signal into a phase component signal in a frequency domain;
calculating a first phase gradient for each of a plurality of frequencies of the phase component signal;
weighting the first phase gradient by one of an amplitude and a power of the frequency to obtain a weighted first phase gradient;
calculating a second phase gradient at a plurality of frequencies as an average of the weighted first phase gradients; and
determining, at a plurality of frequencies, presence of an abrupt change in the input signal based on the first phase gradients and the second phase gradient.

18. The non-transitory computer readable medium according to claim 17, wherein determining the presence of an abrupt change in the input signal includes determining, at a plurality of frequencies, a similarity between the first phase gradient and the second phase gradient.

19. The non-transitory computer readable medium according to claim 17, wherein calculating the second phase gradient includes determining, at a plurality of frequencies, an average value of the weighted first phase gradients at the plurality of frequencies.

20. The non-transitory computer readable medium according to claim 17, wherein the signal processing program causes the computer to execute the method, further including:
calculating an amplitude component signal of the input signal in the frequency domain;
calculating a flatness measure of the amplitude component signal; and determining, at a plurality of frequencies, the presence of an abrupt change in the input signal based on the flatness measure.

\* \* \* \* \*